US007232898B2

(12) United States Patent
Lundgren et al.

(10) Patent No.: US 7,232,898 B2

(45) Date of Patent: Jun. 19, 2007

(54) CHIMERIC IGE POLYPEPTIDES AND HOST CELLS

(75) Inventors: Mats Lundgren, Stockholm (SE); Alexis Fuentes, Uppsala (SE); Ann-Christin Magnusson, Uppsala (SE)

(73) Assignee: Resistentia Pharmaceuticals AB, Uppsala (SE)

( * ) Notice: Subject to any disclaimer, the term of this patent is extended or adjusted under 35 U.S.C. 154(b) by 588 days.

(21) Appl. No.: 10/438,794

(22) Filed: May 15, 2003

(65) Prior Publication Data

US 2004/0038395 A1 Feb. 26, 2004

Related U.S. Application Data

(60) Provisional application No. 60/382,552, filed on May 21, 2002.

(51) Int. Cl.
*C12N 15/11* (2006.01)

(52) U.S. Cl. ................ 536/23.1; 435/69.1; 435/252.1; 435/325; 424/133.1

(58) Field of Classification Search .................... None
See application file for complete search history.

(56) References Cited

U.S. PATENT DOCUMENTS

| | | | |
|---|---|---|---|
| 4,873,191 | A | 10/1989 | Wagner et al. |
| 5,580,859 | A | 12/1996 | Felgner et al. |
| 5,589,466 | A | 12/1996 | Felgner et al. |
| 6,143,559 | A | 11/2000 | Michael et al. |

FOREIGN PATENT DOCUMENTS

| | | |
|---|---|---|
| EP | 0 327 378 | 8/1989 |
| EP | 1 262 491 | 12/2002 |
| EP | 1 009 832 | 6/2003 |
| EP | 0 821 003 | 8/2003 |
| WO | WO 91/11456 | 8/1991 |
| WO | WO 00/25722 | 5/2000 |
| WO | WO 00/32821 | 6/2000 |
| WO | WO 00/67761 | 11/2000 |
| WO | WO 03/015716 | 2/2003 |
| WO | WO 03/15716 | 2/2003 |

OTHER PUBLICATIONS

Margolskee et al. Molecular and Cellular Biology, 1988, 8:2837-2847.*

Walls et al., Nucleic Acids Resarch, 1993, 21:2921-2929.*

Kipriyanov et al., Molecular Biotechnology, 1999, 12:173-201.*

Batista et al., "Characterization and Expression of Alternatively Spliced IgE Heavy Chain Transcripts Produced by Peripheral Blood Lymphocytes," *J. Immunol.,* 1995, 154:209-218.

Knight et al., "Genetic Engineering of Bovine Ig Construction and Characterization of Hapten-Binding Bovine/Murine Chimeric IgE, IgA, IgG1, IgG2, and IgG3 Molecules," *J. Immunol.,* 1988, 140(10):3654-3659.

Nissim et al., "The Use of Mouse/Human IgE Chimeras to Map the FcϵR Binding Site of IgE," *METHODS: A Companion to Methods in Enzymology,* 1995, 8:124-132.

Persson et al., "Generation of a Therapeutic Anti-IgE Response in a Primate Model Through Vaccination," *J. Allergy and Clinical Immunology,* 2003, 111(2):S285.

Vemersson et al., "Generation of therapeutic antibody responses against IgE through vaccination," *FASEB J.,* 2002, 16(8):875-877.

Neuberger, "Expression and regulation of immunoglobulin heavy chain gene transfected into lymphoid cells," *The EMBO Journal,* 1983, 2(8): 1373-1378.

Lo, "Transformation by Iontophoretic Microinjection of DNA: Multiple Integrations Without Tandem Insertions," *Molecular and Cellular Biology,* 1983, 3(10): 1803-1814.

Thomsen et al., "Promoter-regulatory region of the major immediate early gene of human cytomegalovirus," *Proceedings of the National Academy of Sciences of the United States of America,* 1984, 81(3): 659-663.

Van der Putten et al., "Efficient insertion of genes into the mouse germ line via retroviral vectors," *Proceedings of the National Academy of Sciences of the United States of America,* 1985, 82(18): 6148-6152.

Gossler et al., "Transgenesis by means of blastocyst-derived embryonic stem cell lines," *Proceedings of the National Academy of Sciences of the United States of America,* 1986, 83(23): 9065-9069.

Ford et al., "Fusion Tails for the Recovery and Purification of Recombinant Proteins," *Protein Expression and Purification,* 1991, 2(2-3): 95-107.

Thompson et al., "Germ Line Transmission and Expression of a Corrected HPRT Gene Produced by Gene Targeting in Embryonic Stem Cells," *Cell,* 1989, 56(2): 313-321.

Goodwin et al., "The 3'—Flanking Sequence of the Bovine Growth Hormone Gene Contains Novel Elements Required for Efficient and Accurate Polyadenylation," *The Journal of Biological Chemistry,* 1992, 267(23): 16330-16334.

Schnieke, et al., "Human Factor IX Transgenic Sheep Produced by Transfer of Nuclei from Transfected Fetal Firoblasts," *Science,* 1997, 278(5346): 2130-2133.

* cited by examiner

*Primary Examiner*—G. R. Ewoldt
*Assistant Examiner*—Michael Szperka
(74) *Attorney, Agent, or Firm*—Fish & Richardson P.C.

(57) ABSTRACT

The invention provides methods and materials related to expressing chimeric IgE proteins. Specifically, the invention provides nucleic acid vectors, host cells, and methods for producing chimeric IgE polypeptides.

17 Claims, 22 Drawing Sheets

FIG. 2

TCAATATTGGCCATTAGCCATATTATTCATTGGTTATATAGCATAAATCAATATTGGCTATTGGCCATTGCATACGT
TGTATCTATATCATAATATGTACATTTATATTGGCTCATGTCCAATATGACCGCCATGTTGGCATTGATTATTGACT
AGTTATTAATAGTAATCAATTACGGGGTCATTAGTTCATAGCCCATATATGGAGTTCCGCGTTACATAACTTACGGT
AAATGGCCCGCCTGGCTGACCGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACTTGGCAGTACATCAAGTGTAT
CATATGCCAAGTCCGCCCCCTATTGACGTCAATGACGGTAAATGGCCCGCCTGGCATTATGCCCAGTACATGACCTT
ACGGGACTTTCCTACTTGGCAGTACATCTACGTATTAGTCATCGCTATTACCATGGTGATGCGGTTTTGGCAGTACA
CCAATGGGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTGCGATCGCCCGCCCCGTTGACGCAAATGGGCGGT
AGGCGTGTACGGTGGGAGGTCTATATAAGCAGAGCTCGTTTAGTGAACCGTCAGATCACTAGAAGCTTTATTGCGGT
AGTTTATCACAGTTAAATTGCTAACGCAGTCAGTGCTTCTGACACAACAGTCTCGAACTTAAGCTGCAGTGACTCTC
TTAAGGTAGCCTTGCAGAAGTTGGTCGTGAGGCACTGGGCAGGTAAGTATCAAGGTTACAAGACAGGTTTAAGGAGA
CCAATAGAAACTGGGCTTGTCGAGACAGAGAAGACTCTTGCGTTTCTGATAGGCACCTATTGGTCTTACTGACATCC
ACTTTGCCTTTCTCTCCACAGGTGTCCACTCCCAGTTCAATTACAGCTCTTAAGGCTAGAGTACTTAATACGACTCA
CTATAGGCTAGCCTCGAGAATTCACGCGTGGTACCTCTAGAGTCGACCCcgggccgacctcaccatgggatggagct
gtatcatcctcttcttggtagcaacagctacaggtaaggggctcacagtagcaggcttgaggtctggacatatatat
gggtgacaatgacatccactttgcctttctctccacaggtgtgcattcctcgagtactttatctctcccagaaagtg
gccctgtgacaatcatcccacctacagtgaagctcttccactcatcctgtgacccccgaggggatgctcattccacc
atccagctgctctgccttgtctctggcttctccccagccaaggtccatgtgacctggctggtagatggacaggaggc
tgaaaatctctttccctatacaaccagacctaagagggaaggggacagactttttctctacaaagtgaagtcaaca
tcacacagggccagtggatgtcatcaaacacctacacctgccatgtcaagcacaatggcagcatctttgaagacagt
tctagaagatgctcagatgatgagccccggggtgtgattacctacctgatcccacccagtcccctcgacctgtatga
aaatgggactcccaaacttacctgtctggttttggacctggaaagtgaggagaatatcaccgtgacgtgggtccgag
agcgtaagaagtctataggttcggcatcccagaggagtaccaagcaccataatgccacaaccagtatcacctccatc
ttgccagtggatgccaaggactggatcgaaggtgaaggctaccagtgcagagtggaccaccctcactttcccaagcc
cattgtgcgttccatcaccaagcttgctagcccaggcaaacgcttagcccccgaggtatatatgctccctccatctc
cagaggaaacaggaaccactcgcactgtaacctgcctaattcggggtttctacccttctgaaatatctgtccaatgg
ctgtttaataacgaagaggaccacactggacaccatactaccacccgtccccaaaaggaccacggaacggatccttc
cttcttcctctacagccgaatgcttgtcaacaagtctatttgggaaaaaggcaatctcgtcacctgccgtgtggtgc
atgaagccctacctggctcccgcaccctggaaaaaagcctgcattactcagctggtaactaatctcgagcaGGGCGG
CCGCTTCCCTTTAGTGAGGGTTAATGCTTCGAGCAGACATGATAAGATACATTGATGAGTTTGGACAAACCACAACT
AGAATGCAGTGAAAAAAATGCTTTATTTGTGAAATTTGTGATGCTATTGCTTTATTTGTAACCATTATAAGCTGCAA
TAAACAAGTTAACAACAACAATTGCATTCATTTTATGTTTCAGGTTCAGGGGGAGATGTGGGAGGTTTTTTAAAGCA
AGTAAAACCTCTACAAATGTGGTAAAATCCGATAAGGATCGATCCGGGCTGGCGTAATAGCGAAGAGGCCCGCACCG
ATCGCCCTTCCCAACAGTTGCGCAGCCTGAATGGCGAATGGACGCGCCCTGTAGCGGCGCATTAAGCGCGGCGGGTG
TGGTGGTTACGCGCAGCGTGACCGCTACACTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGCTCCCTTTAGGGTTCCGATTTAGTGCTTTACG
GCACCTCGACCCCAAAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATCTCGGTC
TATTCTTTTGATTTATAAGGGATTTTGCCGATTTCGGCCTATTGGTTAAAAAATGAGCTGATTTAACAAAAATTTAA
CGCGAATTTTAACAAAATATTAACGCTTACAATTTCCTGATGCGGTATTTTCTCCTTACGCATCTGTGCGGTATTTC
ACACCGCATACGCGGATCTGCGCAGCACCATGGCCTGAAATAACCTCTGAAAGAGGAACTTGGTTAGGTACCTTCTG
AGGCGGAAAGAACCAGCTGTGGAATGTGTGTCAGTTAGGGTGTGGAAAGTCCCCAGGCTCCCCAGCAGGCAGAAGTA
TGCAAAGCATGCATCTCAATTAGTCAGCAACCAGGTGTGGAAAGTCCCCAGGCTCCCCAGCAGGCAGAAGTATGCAA
AGCATGCATCTCAATTAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCTCGGCCTCTGAGCTAT
TCCAGAAGTAGTGAGGAGGCTTTTTTGGAGGCCTAGGCTTTTGCAAAAAGCTTGATTCTTCTGACACAACAGTCTCG
AACTTAAGGCTAGAGCCACCATGATTGAACAAGATGGATTGCACGCAGGTTCTCCGGCCGCTTGGGTGGAGAGGCTA
TTCGGCTATGACTGGGCACAACAGACAATCGGCTGCTCTGATGCCGCCGTGTTCCGGCTGTCAGCGCAGGGGCGCCC

FIG. 2 (page 2)

GGTTCTTTTTGTCAAGACCGACCTGTCCGGTGCCCTGAATGAACTGCAGGACGAGGCAGCGCGGCTATCGTGGCTGG
CCACGACGGGCGTTCCTTGCGCAGCTGTGCTCGACGTTGTCACTGAAGCGGGAAGGGACTGGCTGCTATTGGGCGAA
GTGCCGGGGCAGGATCTCCTGTCATCTCACCTTGCTCCTGCCGAGAAAGTATCCATCATGGCTGATGCAATGCGGCG
GCTGCATACGCTTGATCCGGCTACCTGCCCATTCGACCACCAAGCGAAACATCGCATCGAGCGAGCACGTACTCGGA
TGGAAGCCGGTCTTGTCGATCAGGATGATCTGGACGAAGAGCATCAGGGGCTCGCGCCAGCCGAACTGTTCGCCAGG
CTCAAGGCGCGCATGCCCGACGGCGAGGATCTCGTCGTGACCCATGGCGATGCCTGCTTGCCGAATATCATGGTGGA
AAATGGCCGCTTTTCTGGATTCATCGACTGTGGCCGGCTGGGTGTGGCGGACCGCTATCAGGACATAGCGTTGGCTA
CCCGTGATATTGCTGAAGAGCTTGGCGGCGAATGGGCTGACCGCTTCCTCGTGCTTTACGGTATCGCCGCTCCCGAT
TCGCAGCGCATCGCCTTCTATCGCCTTCTTGACGAGTTCTTCTGAGCGGGACTCTGGGGTTCGAAATGACCGACCAA
GCGACGCCCAACCTGCCATCACGATGGCCGCAATAAAATATCTTTATTTTCATTACATCTGTGTGTTGGTTTTTTGT
GTGAATCGATAGCGATAAGGATCCGCGTATGGTGCACTCTCAGTACAATCTGCTCTGATGCCGCATAGTTAAGCCAG
CCCCGACACCCGCCAACACCCGCTGACGCGCCCTGACGGGCTTGTCTGCTCCCGGCATCCGCTTACAGACAAGCTGT
GACCGTCTCCGGGAGCTGCATGTGTCAGAGGTTTTCACCGTCATCACCGAAACGCGCGAGACGAAAGGGCCTCGTGA
TACGCCTATTTTTATAGGTTAATGTCATGATAATAATGGTTTCTTAGACGTCAGGTGGCACTTTTCGGGGAAATGTG
CGCGGAACCCCTATTTGTTTATTTTTCTAAATACATTCAAATATGTATCCGCTCATGAGACAATAACCCTGATAAAT
GCTTCAATAATATTGAAAAAGGAAGAGTATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAAGAACGTTTTCCAATGATGAG
CACTTTTAAAGTTCTGCTATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGGCATGACAGTAAGAGAA
TTATGCAGTGCTGCCATAACCATGAGTGATAACACTGCGGCCAACTTACTTCTGACAACGATCGGAGGACCGAAGGA
GCTAACCGCTTTTTTGCACAACATGGGGGATCATGTAACTCGCCTTGATCGTTGGGAACCGGAGCTGAATGAAGCCA
TACCAAACGACGAGCGTGACACCACGATGCCTGTAGCAATGGCAACAACGTTGCGCAAACTATTAACTGGCGAACTA
CTTACTCTAGCTTCCCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTATCATTGCAGCACTGG
GGCCAGATGGTAAGCCCTCCCGTATCGTAGTTATCTACACGACGGGGAGTCAGGCAACTATGGATGAACGAAATAGA
CAGATCGCTGAGATAGGTGCCTCACTGATTAAGCATTGGTAACTGTCAGACCAAGTTTACTCATATATACTTTAGAT
TGATTTAAAACTTCATTTTTAATTTAAAAGGATCTAGGTGAAGATCCTTTTTGATAATCTCATGACCAAAATCCCTT
AACGTGAGTTTTCGTTCCACTGAGCGTCAGACCCCGTAGAAAAGATCAAAGGATCTTCTTGAGATCCTTTTTTTCTG
CGCGTAATCTGCTGCTTGCAAACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTTCTTCTAGTGTAGCCGTAGTTAGGCC
ACCACTTCAAGAACTCTGTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGGAACAGGAGAGCGCACGAGGGAG
CTTCCAGGGGGAAACGCCTGGTATCTTTATAGTCCTGTCGGGTTTCGCCACCTCTGACTTGAGCGTCGATTTTTGTG
ATGCTCGTCAGGGGGGCGGAGCCTATGGAAAAACGCCAGCAACGCGGCCTTTTTACGGTTCCTGGCCTTTTGCTGGC
CTTTTGCTCACATGGCTCGACAGATCT (SEQ ID NO:1)

FIG. 3

```
                              tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 agatgctcag atgatgagcc ccggggtgtg attacctacc tgatcccacc cagtcccctc
1261 gacctgtatg aaaatgggac tcccaaactt acctgtctgg ttttggacct ggaaagtgag
1321 gagaatatca ccgtgacgtg ggtccgagag cgtaagaagt ctataggttc ggcatcccag
1381 aggagtacca agcaccataa tgccacaacc agtatcacct ccatcttgcc agtggatgcc
1441 aaggactgga tcgaaggtga aggctaccag tgcagagtgg accaccctca ctttcccaag
1501 cccattgtgc gttccatcac caagcttgct agcccaggca aacgcttagc ccccgaggta
1561 tatatgctcc ctccatctcc agaggaaaca ggaaccactc gcactgtaac ctgcctaatt
1621 cggggtttct acccttctga aatatctgtc caatggctgt ttaataacga agaggaccac
1681 actggacacc atactaccac ccgtccccaa aaggaccacg gaacggatcc ttccttcttc
1741 ctctacagcc gaatgcttgt caacaagtct atttgggaaa aaggcaatct cgtcacctgc
1801 cgtgtggtgc atgaagccct acctggctcc cgcaccctgg aaaaaagcct gcattactca
1861 gctggtaac (SEQ ID NO:2)
```

FIG. 4

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRRCSDDEP
RGVITYLIPPSPLDLYENGTPKLTCLVLDLESEENITVTWVRERKKSIGSASQRSTKHHNA
TTSITSILPVDAKDWIEGEGYQCRVDHPHFPKPIVRSITKLASPGKRLAPEVYMLPPSPEET
GTTRTVTCLIRGFYPSEISVQWLFNNEEDHTGHHTTTRPQKDHGTDPSFFLYSRMLVNKS
IWEKGNLVTCRVVHEALPGSRTLEKSLHYSAGN (SEQ ID NO:3)

FIG. 6

TCAATATTGGCCATTAGCCATATTATTCATTGGTTATATAGCATAAATCAATATTGGCTATTGGCCATTGCATACGT
TGTATCTATATCATAATATGTACATTTATATTGGCTCATGTCCAATATGACCGCCATGTTGGCATTGATTATTGACT
AGTTATTAATAGTAATCAATTACGGGGTCATTAGTTCATAGCCCATATATGGAGTTCCGCGTTACATAACTTACGGT
AAATGGCCCGCCTGGCTGACCGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACTTGGCAGTACATCAAGTGTAT
CATATGCCAAGTCCGCCCCCTATTGACGTCAATGACGGTAAATGGCCCGCCTGGCATTATGCCCAGTACATGACCTT
ACGGGACTTTCCTACTTGGCAGTACATCTACGTATTAGTCATCGCTATTACCATGGTGATGCGGTTTTGGCAGTACA
CCAATGGGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTGCGATCGCCCGCCCCGTTGACGCAAATGGGCGGT
AGGCGTGTACGGTGGGAGGTCTATATAAGCAGAGCTCGTTTAGTGAACCGTCAGATCACTAGAAGCTTTATTGCGGT
AGTTTATCACAGTTAAATTGCTAACGCAGTCAGTGCTTCTGACACAACAGTCTCGAACTTAAGCTGCAGTGACTCTC
TTAAGGTAGCCTTGCAGAAGTTGGTCGTGAGGCACTGGGCAGGTAAGTATCAAGGTTACAAGACAGGTTTAAGGAGA
CCAATAGAAACTGGGCTTGTCGAGACAGAGAAGACTCTTGCGTTTCTGATAGGCACCTATTGGTCTTACTGACATCC
ACTTTGCCTTTCTCTCCACAGGTGTCCACTCCCAGTTCAATTACAGCTCTTAAGGCTAGAGTACTTAATACGACTCA
CTATAGGCTAGCCTCGAGAATTCACGCGTGGTACCTCTAGAGTCGACCCcgggccgacctcaccatgggatggagct
gtatcatcctcttcttggtagcaacagctacaggtaaggggctcacagtagcaggcttgaggtctggacatatatat
gggtgacaatgacatccactttgcctttctctccacaggtgtgcattcctcgagtactttatctctcccagaaagtg
gccctgtgacaatcatcccacctacagtgaagctcttccactcatcctgtgacccccgaggggatgctcattccacc
atccagctgctctgccttgtctctggcttctccccagccaaggtccatgtgacctggctggtagatggacaggaggc
tgaaaatctctttccctatacaaccagacctaagagggaaggggacagacttttctctacaaagtgaagtcaaca
tcacacagggccagtggatgtcatcaaacacctacacctgccatgtcaagcacaatggcagcatctttgaagacagt
tctagaaagtgtgcagattccaacccgagaggggtgagcgcctacctaagccggcccagcccgttcgacctgttcat
ccgcaagtcgcccacgatcacctgtctggtggtggacctggcacccagcaaggggaccgtgaacctgacctggtccc
gggccagtgggaagcctgtgaaccactccaccagaaaggaggagaagcagcgcaatggcacgttaaccgtcacgtcc
accctgccggtgggcacccgagactggatcgaggggggagacctaccagtgcagggtgacccacccccacctgcccag
ggccctcatgcggtccacgaccaagcttgctagcccaggcaaacgcttagcccccgaggtatatatgctccctccat
ctccagaggaaacaggaaccactcgcactgtaacctgcctaattcggggtttctacccttctgaaatatctgtccaa
tggctgtttaataacgaagaggaccacactggacaccatactaccacccgtccccaaaaggaccacggaacggatcc
ttccttcttcctctacagccgaatgcttgtcaacaagtctatttgggaaaaaggcaatctcgtcacctgccgtgtgg
tgcatgaagccctacctggctcccgcaccctggaaaaaagcctgcattactcagctggtaactaatctcgagcaGGG
CGGCCGCTTCCCTTTAGTGAGGGTTAATGCTTCGAGCAGACATGATAAGATACATTGATGAGTTTGGACAAACCACA
ACTAGAATGCAGTGAAAAAAATGCTTTATTTGTGAAATTTGTGATGCTATTGCTTTATTTGTAACCATTATAAGCTG
CAATAAACAAGTTAACAACAACAATTGCATTCATTTTATGTTTCAGGTTCAGGGGGAGATGTGGGAGGTTTTTTAAA
GCAAGTAAAACCTCTACAAATGTGGTAAAATCCGATAAGGATCGATCCGGGCTGGCGTAATAGCGAAGAGGCCCGCA
CCGATCGCCCTTCCCAACAGTTGCGCAGCCTGAATGGCGAATGGACGCGCCCTGTAGCGGCGCATTAAGCGCGGCGG
GTGTGGTGGTTACGCGCAGCGTGACCGCTACACTTGCCAGCGCCCTAGCGCCCGCTCCTTTCGCTTTCTTCCCTTCC
TTTCTCGCCACGTTCGCCGGCTTTCCCCGTCAAGCTCTAAATCGGGGGCTCCCTTTAGGGTTCCGATTTAGTGCTTT
ACGGCACCTCGACCCCAAAAAACTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGAACAACACTCAACCCTATCTCG
GTCTATTCTTTTGATTTATAAGGGATTTTGCCGATTTCGGCCTATTGGTTAAAAAATGAGCTGATTTAACAAAAATT
TAACGCGAATTTTAACAAAATATTAACGCTTACAATTTCCTGATGCGGTATTTTCTCCTTACGCATCTGTGCGGTAT
TTCACACCGCATACGCGGATCTGCGCAGCACCATGGCCTGAAATAACCTCTGAAAGAGGAACTTGGTTAGGTACCTT
CTGAGGCGGAAAGAACCAGCTGTGGAATGTGTGTCAGTTAGGGTGTGGAAAGTCCCCAGGCTCCCCAGCAGGCAGAA
GTATGCAAAGCATGCATCTCAATTAGTCAGCAACCAGGTGTGGAAAGTCCCCAGGCTCCCCAGCAGGCAGAAGTATG
CAAAGCATGCATCTCAATTAGTCAGCAACCATAGTCCCGCCCCTAACTCCGCCCATCCCGCCCCTAACTCCGCCCAG
TTCCGCCCATTCTCCGCCCCATGGCTGACTAATTTTTTTTATTTATGCAGAGGCCGAGGCCGCCTCGGCCTCTGAGC
TATTCCAGAAGTAGTGAGGAGGCTTTTTTGGAGGCCTAGGCTTTTGCAAAAAGCTTGATTCTTCTGACACAACAGTC

FIG. 6 (page 2)

TCGAACTTAAGGCTAGAGCCACCATGATTGAACAAGATGGATTGCACGCAGGTTCTCCGGCCGCTTGGGTGGAGAGG
CTATTCGGCTATGACTGGGCACAACAGACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGCAGGACGAGGCAGCGCGGCTATCGTGGC
TGGCCACGACGGGCGTTCCTTGCGCAGCTGTGCTCGACGTTGTCACTGAAGCGGGAAGGGACTGGCTGCTATTGGGC
GAAGTGCCGGGGCAGGATCTCCTGTCATCTCACCTTGCTCCTGCCGAGAAAGTATCCATCATGGCTGATGCAATGCG
GCGGCTGCATACGCTTGATCCGGCTACCTGCCCATTCGACCACCAAGCGAAACATCGCATCGAGCGAGCACGTACTC
GGATGGAAGCCGGTCTTGTCGATCAGGATGATCTGGACGAAGAGCATCAGGGGCTCGCGCCAGCCGAACTGTTCGCC
AGGCTCAAGGCGCGCATGCCCGACGGCGAGGATCTCGTCGTGACCCATGGCGATGCCTGCTTGCCGAATATCATGGT
GGAAAATGGCCGCTTTTCTGGATTCATCGACTGTGGCCGGCTGGGTGTGGCGGACCGCTATCAGGACATAGCGTTGG
CTACCCGTGATATTGCTGAAGAGCTTGGCGGCGAATGGGCTGACCGCTTCCTCGTGCTTTACGGTATCGCCGCTCCC
GATTCGCAGCGCATCGCCTTCTATCGCCTTCTTGACGAGTTCTTCTGAGCGGGACTCTGGGGTTCGAAATGACCGAC
CAAGCGACGCCCAACCTGCCATCACGATGGCCGCAATAAAATATCTTTATTTTCATTACATCTGTGTGTTGGTTTTT
TGTGTGAATCGATAGCGATAAGGATCCGCGTATGGTGCACTCTCAGTACAATCTGCTCTGATGCCGCATAGTTAAGC
CAGCCCCGACACCCGCCAACACCCGCTGACGCGCCCTGACGGGCTTGTCTGCTCCCGGCATCCGCTTACAGACAAGC
TGTGACCGTCTCCGGGAGCTGCATGTGTCAGAGGTTTTCACCGTCATCACCGAAACGCGCGAGACGAAAGGGCCTCG
TGATACGCCTATTTTTATAGGTTAATGTCATGATAATAATGGTTTCTTAGACGTCAGGTGGCACTTTTCGGGGAAAT
GTGCGCGGAACCCCTATTTGTTTATTTTTCTAAATACATTCAAATATGTATCCGCTCATGAGACAATAACCCTGATA
AATGCTTCAATAATATTGAAAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAGCAACTCGGTCGCCGCA
TACACTATTCTCAGAATGACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTGGGAACCGGAGCTGAATGAAG
CCATACCAAACGACGAGCGTGACACCACGATGCCTGTAGCAATGGCAACAACGTTGCGCAAACTATTAACTGGCGAA
CTACTTACTCTAGCTTCCCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCGCGGTATCATTGCAGCAC
TGGGGCCAGATGGTAAGCCCTCCCGTATCGTAGTTATCTACACGACGGGGAGTCAGGCAACTATGGATGAACGAAAT
AGACAGATCGCTGAGATAGGTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAGGATCTTCTTGAGATCCTTTTTTT
CTGCGCGTAATCTGCTGCTTGCAAACAAAAAAACCACCGCTACCAGCGGTGGTTTGTTTGCCGGATCAAGAGCTACC
AACTCTTTTTCCGAAGGTAACTGGCTTCAGCAGAGCGCAGATACCAAATACTGTTCTTCTAGTGTAGCCGTAGTTAG
GCCACCACTTCAAGAACTCTGTAGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAGGCGCAGCGGTCGGGCTGAACGGG
GGGTTCGTGCACACAGCCCAGCTTGGAGCGAACGACCTACACCGAACTGAGATACCTACAGCGTGAGCTATGAGAAA
GCGCCACGCTTCCCGAAGGGAGAAAGGCGGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTTTTTACGGTTCCTGGCCTTTTGCT
GGCCTTTTGCTCACATGGCTCGACAGATCT (SEQ ID NO: 4)

FIG. 7

```
                         tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 aagtgtgcag attccaaccc gagaggggtg agcgcctacc taagccggcc cagcccgttc
1261 gacctgttca tccgcaagtc gcccacgatc acctgtctgg tggtggacct ggcacccagc
1321 aaggggaccg tgaacctgac ctggtcccgg gccagtggga agcctgtgaa ccactccacc
1381 agaaaggagg agaagcagcg caatggcacg ttaaccgtca cgtccaccct gccggtgggc
1441 acccgagact ggatcgaggg ggagacctac cagtgcaggg tgacccaccc ccacctgccc
1501 agggccctca tgcggtccac gaccaagctt gctagcccag gcaaacgctt agcccccgag
1561 gtatatatgc tccctccatc tccagaggaa acaggaacca ctcgcactgt aacctgccta
1621 attcggggtt tctacccttc tgaaatatct gtccaatggc tgtttaataa cgaagaggac
1681 cacactggac accatactac cacccgtccc caaaaggacc acggaacgga tccttccttc
1741 ttcctctaca gccgaatgct tgtcaacaag tctatttggg aaaaaggcaa tctcgtcacc
1801 tgccgtgtgg tgcatgaagc cctacctggc tcccgcaccc tggaaaaaag cctgcattac
1861 tcagctggta ac (SEQ ID NO:5)
```

FIG. 8

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRKCADSN
PRGVSAYLSRPSPFDLFIRKSPTITCLVVDLAPSKGTVNLTWSRASGKPVNHSTRKEEKQ
RNGTLTVTSTLPVGTRDWIEGETYQCRVTHPHLPRALMRSTTKLASPGKRLAPEVYMLP
PSPEETGTTRTVTCLIRGFYPSEISVQWLFNNEEDHTGHHTTTRPQKDHGTDPSFFLYSR
MLVNKSIWEKGNLVTCRVVHEALPGSRTLEKSLHYSAGN
(SEQ ID NO:6)

FIG. 9

```
                         tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 agatgctcag atgatgagcc ccggggtgtg attacctacc tgatcccacc cagtcccctc
1261 gacctgtatg aaaatgggac tcccaaactt acctgtctgg ttttggacct ggaaagtgag
1321 gagaatatca ccgtgacgtg ggtccgagag cgtaagaagt ctataggttc ggcatcccag
1381 aggagtacca agcaccataa tgccacaacc agtatcacct ccatcttgcc agtggatgcc
1441 aaggactgga tcgaaggtga aggctaccag tgcagagtgg accaccctca ctttcccaag
1501 cccattgtgc gttccatcac caagcttatc gatctcccag aaagtggccc tgtgacaatc
1561 atcccaccta cagtgaagct cttccactca tcctgtgacc cccgagggga tgctcattcc
1621 accatccagc tgctctgcct tgtctctggc ttctccccag ccaaggtcca tgtgacctgg
1681 ctggtagatg gacaggaggc tgaaaatctc tttccctata caaccagacc taagagggaa
1741 gggggacaga ctttttctct acaaagtgaa gtcaacatca cacagggcca gtggatgtca
1801 tcaaacacct acacctgcca tgtcaagcac aatggcagca tctttgaaga cagttctaga
1861 agatgctcag atgatgagcc ccggggtgtg attacctacc tgatcccacc cagtcccctc
1921 gacctgtatg aaaatgggac tcccaaactt acctgtctgg ttttggacct ggaaagtgag
1981 gagaatatca ccgtgacgtg ggtccgagag cgtaagaagt ctataggttc ggcatcccag
2041 aggagtacca agcaccataa tgccacaacc agtatcacct ccatcttgcc agtggatgcc
2101 aaggactgga tcgaaggtga aggctaccag tgcagagtgg accaccctca ctttcccaag
2161 cccattgtgc gttccatcac cgctagccca ggcaaacgct tagcccccga ggtatatatg
2221 ctccctccat ctccagagga aacaggaacc actcgcactg taacctgcct aattcggggt
2281 ttctaccctt ctgaaatatc tgtccaatgg ctgtttaata acgaagagga ccacactgga
2341 caccatacta ccacccgtcc ccaaaaggac cacggaacgg atccttcctt cttcctctac
2401 agccgaatgc ttgtcaacaa gtctatttgg gaaaaaggca atctcgtcac ctgccgtgtg
2461 gtgcatgaag ccctacctgg ctcccgcacc ctggaaaaaa gcctgcatta ctcagctggt
2521 aac (SEQ ID NO:7)
```

FIG. 10

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRRCSDDEP
RGVITYLIPPSPLDLYENGTPKLTCLVLDLESEENITVTWVRERKKSIGSASQRSTKHHNA
TTSITSILPVDAKDWIEGEGYQCRVDHPHFPKPIVRSITKLIDLPESGPVTIIPPTVKLFHSS
CDPRGDAHSTIQLLCLVSGFSPAKVHVTWLVDGQEAENLFPYTTRPKREGGQTFSLQSE
VNITQGQWMSSNTYTCHVKHNGSIFEDSSRRCSDDEPRGVITYLIPPSPLDLYENGTPKL
TCLVLDLESEENITVTWVRERKKSIGSASQRSTKHHNATTSITSILPVDAKDWIEGEGYQ
CRVDHPHFPKPIVRSITASPGKRLAPEVYMLPPSPEETGTTRTVTCLIRGFYPSEISVQWLF
NNEEDHTGHITTTRPQKDHGTDPSFFLYSRMLVNKSIWEKGNLVTCRVVHEALPGSRT
LEKSLHYSAGN (SEQ ID NO:8)

FIG. 11

```
                         tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 aagtgtgcag attccaaccc gagaggggtg agcgcctacc taagccggcc cagcccgttc
1261 gacctgttca tccgcaagtc gcccacgatc acctgtctgg tggtggacct ggcacccagc
1321 aaggggaccg tgaacctgac ctggtccgag gcccaaggga agcctgtgaa ccactccacc
1381 agaaaggagg agaagcagcg caatggcacg ttaaccgtca cgtccaccct gccggtgggc
1441 acccgagact ggatcgaggg gcgtacgtac cagtgcaggg tgacccaccc ccacctgccc
1501 agggccctca tgcggtccac gaccaagctt atcgatatcc cagaaagtgg ccctgtgaca
1561 atcatcccac ctacagtgaa gctcttccac tcatcctgtg acccccgagg ggatgctcat
1621 tccaccatcc agctgctctg ccttgtctct ggcttctccc cagccaaggt ccatgtgacc
1681 tggctggtag atggacagga ggctgaaaat ctctttccct atacaaccag acctaagagg
1741 gaagggggac agactttttc tctacaaagt gaagtcaaca tcacacaggg ccagtggatg
1801 tcatcaaaca cctacacctg ccatgtcaag cacaatggca gcatctttga agacagttct
1861 agaaagtgtg cagattccaa cccgagaggg gtgagcgcct acctaagccg gcccagcccg
1921 ttcgacctgt tcatccgcaa gtcgcccacg atcacctgtc tggtggtgga cctggcaccc
1981 agcaagggga ccgtgaacct gacctggtcc gaggcccaag ggaagcctgt gaaccactcc
2041 accagaaagg aggagaagca gcgcaatggc acgttaaccg tcacgtccac cctgccggtg
2101 ggcacccgag actggatcga ggggcgtacg taccagtgca gggtgaccca cccccacctg
2161 cccagggccc tcatgcggtc cacgaccgct agcccaggca aacgcttagc cccgaggtta
2221 tatatgctcc ctccatctcc agaggaaaca ggaaccactc gcactgtaac ctgcctaatt
2281 cggggtttct acccttctga aatatctgtc caatggctgt ttaataacga agaggaccac
2341 actggacacc atactaccac ccgtccccaa aaggaccacg gaacggatcc ttccttcttc
2401 ctctacagcc gaatgcttgt caacaagtct atttgggaaa aaggcaatct cgtcacctgc
2461 cgtgtggtgc atgaagccct acctggctcc cgcaccctgg aaaaaagcct gcattactca
2521 gctggtaacg gatcaggaca ccatcaccat caccat (SEQ ID NO:9)
```

FIG. 12

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRKCADSN
PRGVSAYLSRPSPFDLFIRKSPTITCLVVDLAPSKGTVNLTWSRASGKPVNHSTRKEEKQ
RNGTLTVTSTLPVGTRDWIEGETYQCRVTHPHLPRALMRSTTKLIDIPESGPVTIIPPTVKL
FHSSCDPRGDAHSTIQLLCLVSGFSPAKVHVTWLVDGQEAENLFPYTTRPKREGGQTFS
LQSEVNITQGQWMSSNTYTCHVKHNGSIFEDSSRKCADSNPRGVSAYLSRPSPFDLFIRK
SPTITCLVVDLAPSKGTVNLTWSRASGKPVNHSTRKEEKQRNGTLTVTSTLPVGTRDWI
EGETYQCRVTHPHLPRALMRSTTASPGKRLAPEVYMLPPSPEETGTTRTVTCLIRGFYPS
EISVQWLFNNEEDHTGHHTTTRPQKDHGTDPSFFLYSRMLVNKSIWEKGNLVTCRVVH
EALPGSRTLEKSLHYSAGNGSGHHHHHH (SEQ ID NO:10)

FIG. 13

```
                  tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 aagtgtgcag attccaaccc gagaggggtg agcgcctacc taagccggcc cagcccgttc
1261 gacctgttca tccgcaagtc gcccacgatc acctgtctgg tggtggacct ggcacccagc
1321 aaggggaccg tgaacctgac ctggtccgag gcccaaggga agcctgtgaa ccactccacc
1381 agaaaggagg agaagcagcg caatggcacg ttaaccgtca cgtccaccct gccggtgggc
1441 acccgagact ggatcgaggg gcgtacgtac cagtgcaggg tgacccaccc ccacctgccc
1501 agggccctca tgcggtccac gaccaagctt atcgatatcc cagaaagtgg ccctgtgaca
1561 atcatcccac ctacagtgaa gctcttccac tcatcctgtg acccccgagg ggatgctcat
1621 tccaccatcc agctgctctg ccttgtctct ggcttctccc cagccaaggt ccatgtgacc
1681 tggctggtag atggacagga ggctgaaaat ctctttccct atacaaccag acctaagagg
1741 gaagggggac agactttttc tctacaaagt gaagtcaaca tcacacaggg ccagtggatg
1801 tcatcaaaca cctacacctg ccatgtcaag cacaatggca gcatctttga agacagttct
1861 agaaagtgtg cagattccaa cccgagaggg gtgagcgcct acctaagccg gcccagcccg
1921 ttcgacctgt tcatccgcaa gtcgcccacg atcacctgtc tggtggtgga cctggcaccc
1981 agcaagggga ccgtgaacct gacctggtcc gaggcccaag ggaagcctgt gaaccactcc
2041 accagaaagg aggagaagca gcgcaatggc acgttaaccg tcacgtccac cctgccggtg
2101 ggcacccgag actggatcga ggggcgtacg taccagtgca gggtgaccca cccccacctg
2161 cccagggccc tcatgcggtc cacgaccgct agcccaggca aacgcttagc cccccgaggta
2221 tatatgctcc ctccatctcc agaggaaaca ggaaccactc gcactgtaac ctgcctaatt
2281 cggggtttct acccttctga aatatctgtc caatggctgt ttaataacga agaggaccac
2341 actggacacc atactaccac ccgtccccaa aaggaccacg gaacggatcc ttccttcttc
2401 ctctacagcc gaatgcttgt caacaagtct atttgggaaa aaggcaatct cgtcacctgc
2461 cgtgtggtgc atgaagccct acctggctcc cgcaccctgg aaaaaagcct gcattactca
2521 gctggtaac (SEQ ID NO:11)
```

FIG. 14

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRKCADSN
PRGVSAYLSRPSPFDLFIRKSPTITCLVVDLAPSKGTVNLTWSRASGKPVNHSTRKEEKQ
RNGTLTVTSTLPVGTRDWIEGETYQCRVTHPHLPRALMRSTTKLIDIPESGPVTIIPPTVKL
FHSSCDPRGDAHSTIQLLCLVSGFSPAKVHVTWLVDGQEAENLFPYTTRPKREGGQTFS
LQSEVNITQGQWMSSNTYTCHVKHNGSIFEDSSRKCADSNPRGVSAYLSRPSPFDLFIRK
SPTITCLVVDLAPSKGTVNLTWSRASGKPVNHSTRKEEKQRNGTLTVTSTLPVGTRDWI
EGETYQCRVTHPHLPRALMRSTTASPGKRLAPEVYMLPPSPEETGTTRTVTCLIRGFYPS
EISVQWLFNNEEDHTGHHTTTRPQKDHGTDPSFFLYSRMLVNKSIWEKGNLVTCRVVH
EALPGSRTLEKSLHYSAGN (SEQ ID NO:12)

FIG. 15

```
                             tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 aagtgtgcag attccaaccc gagaggggtg agcgcctacc taagccggcc cagcccgttc
1261 gacctgttca tccgcaagtc gcccacgatc acctgtctgg tggtggacct ggcacccagc
1321 aaggggaccg tgaacctgac ctggtcccgg gccagtggga agcctgtgaa ccactccacc
1381 agaaaggagg agaagcagcg caatggcacg ttaaccgtca cgtccaccct gccggtgggc
1441 acccgagact ggatcgaggg ggagacctac cagtgcaggg tgacccaccc ccacctgccc
1501 agggccctca tgcggtccac gaccaagctt gctagcccag gcaaacgctt agcccccgag
1561 gtatatatgc tccctccatc tccagaggaa acaggaacca ctcgcactgt aacctgccta
1621 attcggggtt tctacccttc tgaaatatct gtccaatggc tgtttaataa cgaagaggac
1681 cacactggac accatactac cacccgtccc caaaaggacc acggaacgga tccttccttc
1741 ttcctctaca gccgaatgct tgtcaacaag tctatttggg aaaaaggcaa tctcgtcacc
1801 tgccgtgtgg tgcatgaagc cctacctggc tcccgcaccc tggaaaaaag cctgcattac
1861 tcagctggta acggatcagg acaccatcac catcaccat (SEQ ID NO:13)
```

FIG. 16

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRKCADSN
PRGVSAYLSRPSPFDLFIRKSPTITCLVVDLAPSKGTVNLTWSRASGKPVNHSTRKEEKQ
RNGTLTVTSTLPVGTRDWIEGETYQCRVTHPHLPRALMRSTTKLASPGKRLAPEVYMLP
PSPEETGTTRTVTCLIRGFYPSEISVQWLFNNEEDHTGHHTTTRPQKDHGTDPSFFLYSR
MLVNKSIWEKGNLVTCRVVHEALPGSRTLEKSLHYSAGNGSGHHHHHH (SEQ ID
NO:14)

FIG. 17

```
                      tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 aagtgtgcag attccaaccc gagaggggtg agcgcctacc taagccggcc cagcccgttc
1261 gacctgttca tccgcaagtc gcccacgatc acctgtctgg tggtggacct ggcacccagc
1321 aaggggaccg tgaacctgac ctggtcccgg gccagtggga agcctgtgaa ccactccacc
1381 agaaaggagg agaagcagcg caatggcacg ttaaccgtca cgtccaccct gccggtgggc
1441 acccgagact ggatcgaggg ggagacctac cagtgcaggg tgacccaccc ccacctgccc
1501 agggccctca tgcggtccac gaccaagctt atcgatatcc cagaaagtgg ccctgtgaca
1561 atcatcccac ctacagtgaa gctcttccac tcatcctgtg acccccgagg ggatgctcat
1621 tccaccatcc agctgctctg ccttgtctct ggcttctccc cagccaaggt ccatgtgacc
1681 tggctggtag atggacagga ggctgaaaat ctctttccct atacaaccag acctaagagg
1741 gaagggggac agactttttc tctacaaagt gaagtcaaca tcacacaggg ccagtggatg
1801 tcatcaaaca cctacacctg ccatgtcaag cacaatggca gcatctttga agacagttct
1861 agaaagtgtg cagattccaa cccgagaggg gtgagcgcct acctaagccg gcccagcccg
1921 ttcgacctgt tcatccgcaa gtcgcccacg atcacctgtc tggtggtgga cctggcaccc
1981 agcaagggga ccgtgaacct gacctggtcc cgggccagtg ggaagcctgt gaaccactcc
2041 accagaaagg aggagaagca gcgcaatggc acgttaaccg tcacgtccac cctgccggtg
2101 ggcacccgag actggatcga gggggagacc taccagtgca gggtgaccca cccccacctg
2161 cccagggccc tcatgcggtc cacgaccgct agcccaggca aacgcttagc ccccgaggta
2221 tatatgctcc ctccatctcc agaggaaaca ggaaccactc gcactgtaac ctgcctaatt
2281 cggggtttct acccttctga aatatctgtc caatggctgt ttaataacga agaggaccac
2341 actggacacc atactaccac ccgtccccaa aaggaccacg gaacggatcc ttccttcttc
2401 ctctacagcc gaatgcttgt caacaagtct atttgggaaa aaggcaatct cgtcacctgc
2461 cgtgtggtgc atgaagccct acctggctcc cgcaccctgg aaaaaagcct gcattactca
2521 gctggtaac (SEQ ID NO:15)
```

FIG. 18

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRKCADSN
PRGVSAYLSRPSPFDLFIRKSPTITCLVVDLAPSKGTVNLTWSRASGKPVNHSTRKEEKQ
RNGTLTVTSTLPVGTRDWIEGETYQCRVTHPHLPRALMRSTTKLIDIPESGPVTIIPPTVKL
FHSSCDPRGDAHSTIQLLCLVSGFSPAKVHVTWLVDGQEAENLFPYTTRPKREGGQTFS
LQSEVNITQGQWMSSNTYTCHVKHNGSIFEDSSRKCADSNPRGVSAYLSRPSPFDLFIRK
SPTITCLVVDLAPSKGTVNLTWSRASGKPVNHSTRKEEKQRNGTLTVTSTLPVGTRDWI
EGETYQCRVTHPHLPRALMRSTTASPGKRLAPEVYMLPPSPEETGTTRTVTCLIRGFYPS
EISVQWLFNNEEDHTGHHTTTRPQKDHGTDPSFFLYSRMLVNKSIWEKGNLVTCRVVH
EALPGSRTLEKSLHYSAGN (SEQ ID NO:16)

FIG. 19

```
                     tc gagtacttta tctctcccag aaagtggccc tgtgacaatc
 901 atcccaccta cagtgaagct cttccactca tcctgtgacc cccgagggga tgctcattcc
 961 accatccagc tgctctgcct tgtctctggc ttctccccag ccaaggtcca tgtgacctgg
1021 ctggtagatg gacaggaggc tgaaaatctc tttccctata caaccagacc taagagggaa
1081 gggggacaga ctttttctct acaaagtgaa gtcaacatca cacagggcca gtggatgtca
1141 tcaaacacct acacctgcca tgtcaagcac aatggcagca tctttgaaga cagttctaga
1201 aagtgtgcag attccaaccc gagaggggtg agcgcctacc taagccggcc cagcccgttc
1261 gacctgttca tccgcaagtc gcccacgatc acctgtctgg tggtggacct ggcacccagc
1321 aaggggaccg tgaacctgac ctggtcccgg gccagtggga agcctgtgaa ccactccacc
1381 agaaaggagg agaagcagcg caatggcacg ttaaccgtca cgtccaccct gccggtgggc
1441 acccgagact ggatcgaggg ggagacctac cagtgcaggg tgacccaccc ccacctgccc
1501 agggccctca tgcggtccac gaccaagctt atcgatatcc cagaaagtgg ccctgtgaca
1561 atcatcccac ctacagtgaa gctcttccac tcatcctgtg acccccgagg ggatgctcat
1621 tccaccatcc agctgctctg ccttgtctct ggcttctccc cagccaaggt ccatgtgacc
1681 tggctggtag atggacagga ggctgaaaat ctctttccct atacaaccag acctaagagg
1741 gaagggggac agactttttc tctacaaagt gaagtcaaca tcacacaggg ccagtggatg
1801 tcatcaaaca cctacacctg ccatgtcaag cacaatggca gcatctttga agacagttct
1861 agaaagtgtg cagattccaa cccgagaggg gtgagcgcct acctaagccg gcccagcccg
1921 ttcgacctgt tcatccgcaa gtcgcccacg atcacctgtc tggtggtgga cctggcaccc
1981 agcaagggga ccgtgaacct gacctggtcc cgggccagtg ggaagcctgt gaaccactcc
2041 accagaaagg aggagaagca gcgcaatggc acgttaaccg tcacgtccac cctgccggtg
2101 ggcacccgag actggatcga gggggagacc taccagtgca gggtgaccca cccccacctg
2161 cccagggccc tcatgcggtc cacgaccgct agcccaggca aacgcttagc cccgaggta
2221 tatatgctcc ctccatctcc agaggaaaca ggaaccactc gcactgtaac ctgcctaatt
2281 cggggtttct acccttctga aatatctgtc caatggctgt ttaataacga agaggaccac
2341 actggacacc atactaccac ccgtccccaa aaggaccacg gaacggatcc ttccttcttc
2401 ctctacagcc gaatgcttgt caacaagtct atttgggaaa aaggcaatct cgtcacctgc
2461 cgtgtggtgc atgaagccct acctggctcc cgcaccctgg aaaaaagcct gcattactca
2521 gctggtaacg gatcaggaca ccatcaccat caccat (SEQ ID NO:17)
```

FIG. 20

SSTLSLPESGPVTIIPPTVKLFHSSCDPRGDAHSTIQLLCLVSGFSPAKVHVTWLVDGQEA
ENLFPYTTRPKREGGQTFSLQSEVNITQGQWMSSNTYTCHVKHNGSIFEDSSRKCADSN
PRGVSAYLSRPSPFDLFIRKSPTITCLVVDLAPSKGTVNLTWSRASGKPVNHSTRKEEKQ
RNGTLTVTSTLPVGTRDWIEGETYQCRVTHPHLPRALMRSTTKLIDIPESGPVTIIPPTVKL
FHSSCDPRGDAHSTIQLLCLVSGFSPAKVHVTWLVDGQEAENLFPYTTRPKREGGQTFS
LQSEVNITQGQWMSSNTYTCHVKHNGSIFEDSSRKCADSNPRGVSAYLSRPSPFDLFIRK
SPTITCLVVDLAPSKGTVNLTWSRASGKPVNHSTRKEEKQRNGTLTVTSTLPVGTRDWI
EGETYQCRVTHPHLPRALMRSTTASPGKRLAPEVYMLPPSPEETGTTRTVTCLIRGFYPS
EISVQWLFNNEEDHTGHHTTTRPQKDHGTDPSFFLYSRMLVNKSIWEKGNLVTCRVVH
EALPGSRTLEKSLHYSAGNGSGHHHHHH (SEQ ID NO:18)

CHIMERIC IGE POLYPEPTIDES AND HOST CELLS

RELATED APPLICATIONS

This application claims the benefit of U.S. Provisional Application Ser. No. 60/382,552, filed May 21, 2002.

BACKGROUND

1. Technical Field

The invention relates to methods and materials involved in expressing and purifying recombinant chimeric IgE polypeptides.

2. Background Information

Generating a vaccine to treat IgE-induced hypersensitivity conditions such as food, dander, and pollen allergies, asthma, and eczema requires large quantities of a chimeric IgE polypeptide effective to induce the production of anti-self IgE antibodies when administered to a mammal. Recombinant DNA technology is widely used in medicine, diagnostics, agriculture, and related fields to produce large amounts of a desired polypeptide quickly and cost-effectively. Appropriately designed genetic constructs can permit a polypeptide to be produced by a variety of prokaryotic and eukaryotic organisms, including bacteria, yeast, insect larvae, insect cells, and mammalian cells. The organisms and nucleic acid vectors used depend on such factors as structure and function of the desired polypeptide, post-translational modification requirements, purification requirements and restrictions, required yields, and the purified polypeptide's intended application.

SUMMARY

The invention provides methods and materials related to expressing IgE polypeptides such as chimeric IgE polypeptides. Specifically, the invention provides nucleic acid vectors, host cells, and methods for producing chimeric IgE polypeptides. When administered to a mammal, the chimeric IgE polypeptides provided herein can reduce the IgE antibody effects of IgE-related diseases such as asthma, allergies, and eczema.

In one aspect, the invention provides a host cell having a nucleic acid vector, wherein the nucleic acid vector includes a cytomegalovirus promoter, an Ig leader sequence, an insert sequence, and a SV40 late polyadenylation sequence such that the cytomegalovirus promoter is upstream from and operably linked to the insert sequence, the Ig leader sequence is downstream from the cytomegalovirus promoter and upstream from and operably linked to the insert sequence, the SV40 late polyadenylation sequence is downstream from and operably linked to the insert sequence, and the insert sequence encodes a chimeric IgE polypeptide. The insert sequence can have a sequence selected from the group consisting of SEQ ID NO:2, SEQ ID NO:5, SEQ ID NO:7, SEQ ID NO:9, SEQ ID NO:11, SEQ ID NO:13, SEQ ID NO:15, and SEQ ID NO:17. The chimeric IgE polypeptide encoded by the insert sequence can have a sequence selected from the group consisting of SEQ ID NO:3, SEQ ID NO:6, SEQ ID NO:8, SEQ ID NO:10, SEQ ID NO:12, SEQ ID NO:14, SEQ ID NO:16, and SEQ ID NO:18. The host cell can be a JM109, DH5α, NS0, HeLa, BHK-21, COS-7, Sf9, or CHO cell, or descendants therefrom that include a chimeric IgE polypeptide.

In another aspect, the invention provides a method for producing a chimeric IgE polypeptide by culturing a eukaryotic cell having a vector including a cytomegalovirus promoter, an Ig leader sequence, an insert sequence, and a SV40 late polyadenylation sequence such that the cytomegalovirus promoter is upstream from and operably linked to the insert sequence, the Ig leader sequence is downstream from the cytomegalovirus promoter and upstream from and operably linked to the insert sequence, the SV40 late polyadenylation sequence is downstream from and operably linked to the insert sequence, and the insert sequence encodes a chimeric IgE polypeptide; and recovering the chimeric IgE polypeptide from the culture. Again, the insert sequence can have a sequence selected from the group consisting of SEQ ID NO:2, SEQ ID NO:5, SEQ ID NO:7, SEQ ID NO:9, SEQ ID NO:11, SEQ ID NO:13, SEQ ID NO:15, and SEQ ID NO:17. Also, the chimeric IgE polypeptide can have a sequence selected from the group consisting of SEQ ID NO:3, SEQ ID NO:6, SEQ ID NO:8, SEQ ID NO:10, SEQ ID NO:12, SEQ ID NO:14, SEQ ID NO:16, and SEQ ID NO:18. Further, the host cell can be a JM109, DH5α, NS0, HeLa, BHK-21, COS-7, Sf9, or CHO cell.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 is the sequence of the nucleic acid vector designated pRES-ORO (SEQ ID NO:1)

FIG. 3 is the sequence of the insert sequence designated ORO (SEQ ID NO:2).

FIG. 4 is the sequence of the polypeptide designated ORO (SEQ ID NO:3).

FIG. 6 is the sequence of the nucleic acid vector designated pRES-OSO (SEQ ID NO:4)

FIG. 7 is the sequence of the insert sequence designated OSO (SEQ ID NO:5).

FIG. 8 is the sequence of the polypeptide designated OSO (SEQ ID NO:6).

FIG. 9 is the sequence of the insert sequence designated ORORO (SEQ ID NO:7).

FIG. 10 is the sequence of the polypeptide designated ORORO (SEQ ID NO:8).

FIG. 11 is the sequence of the insert sequence designated modOSOSO-H (SEQ ID NO:9).

FIG. 12 is the sequence of the polypeptide designated modOSOSO-H (SEQ ID NO:10).

FIG. 13 is the sequence of the insert sequence designated modOSOSO (SEQ ID NO:11).

FIG. 14 is the sequence of the polypeptide designated modOSOSO (SEQ ID NO:12).

FIG. 15 is the sequence of the insert sequence designated OSO-H (SEQ ID NO:13).

FIG. 16 is the sequence of the polypeptide designated OSO-H (SEQ ID NO:14).

FIG. 17 is the sequence of the insert sequence designated OSOSO (SEQ ID NO:15).

FIG. 18 is the sequence of the polypeptide designated OSOSO (SEQ ID NO:16).

FIG. 19 is the sequence of the insert sequence designated OSOSO-H (SEQ ID NO:17).

FIG. 20 is the sequence of the polypeptide designated OSOSO-H (SEQ ID NO:18).

DETAILED DESCRIPTION

Figure 1:
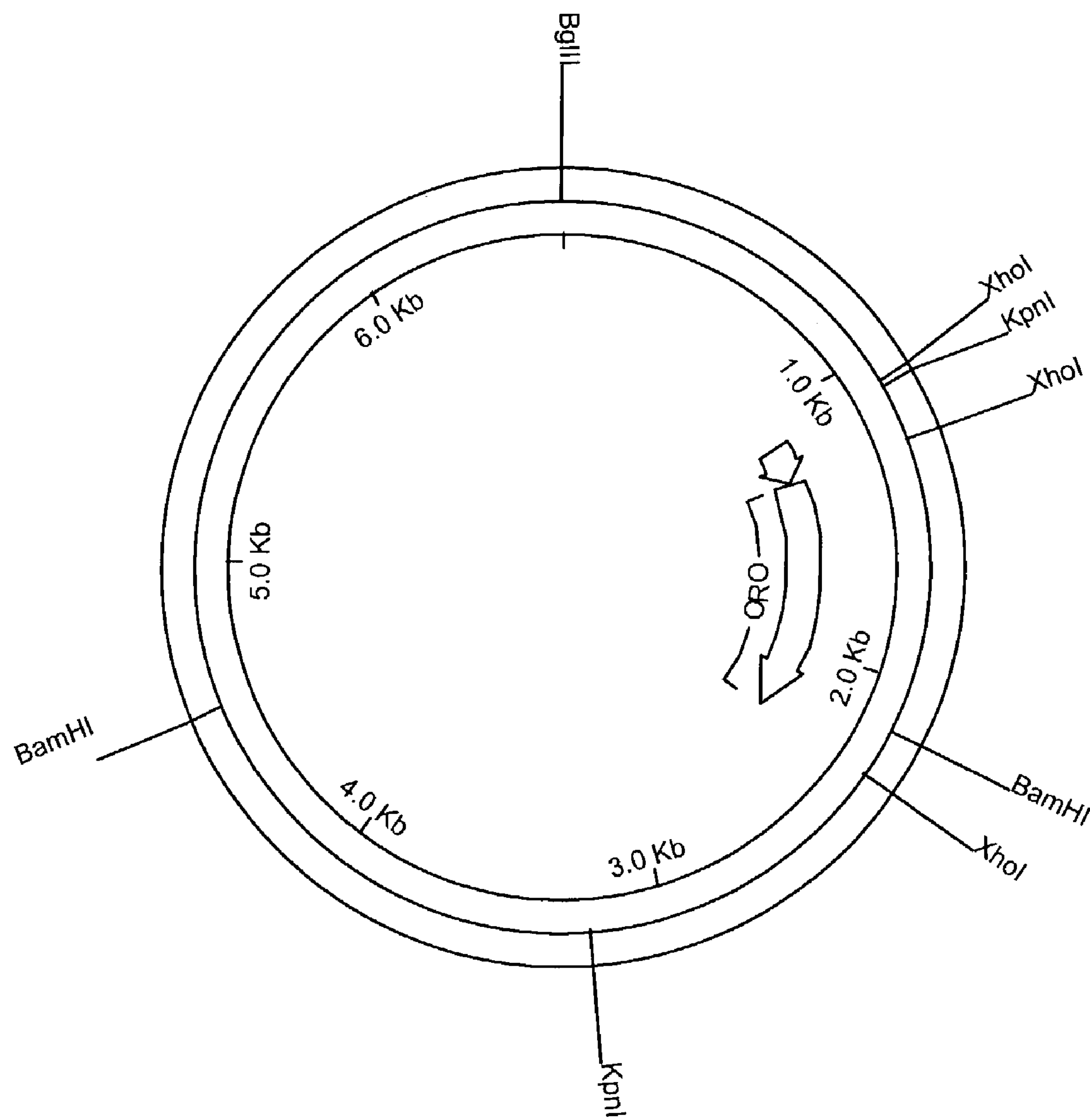
FIG. 1 is a diagram of the nucleic acid vector designated pRES-ORO.
Figure 5:
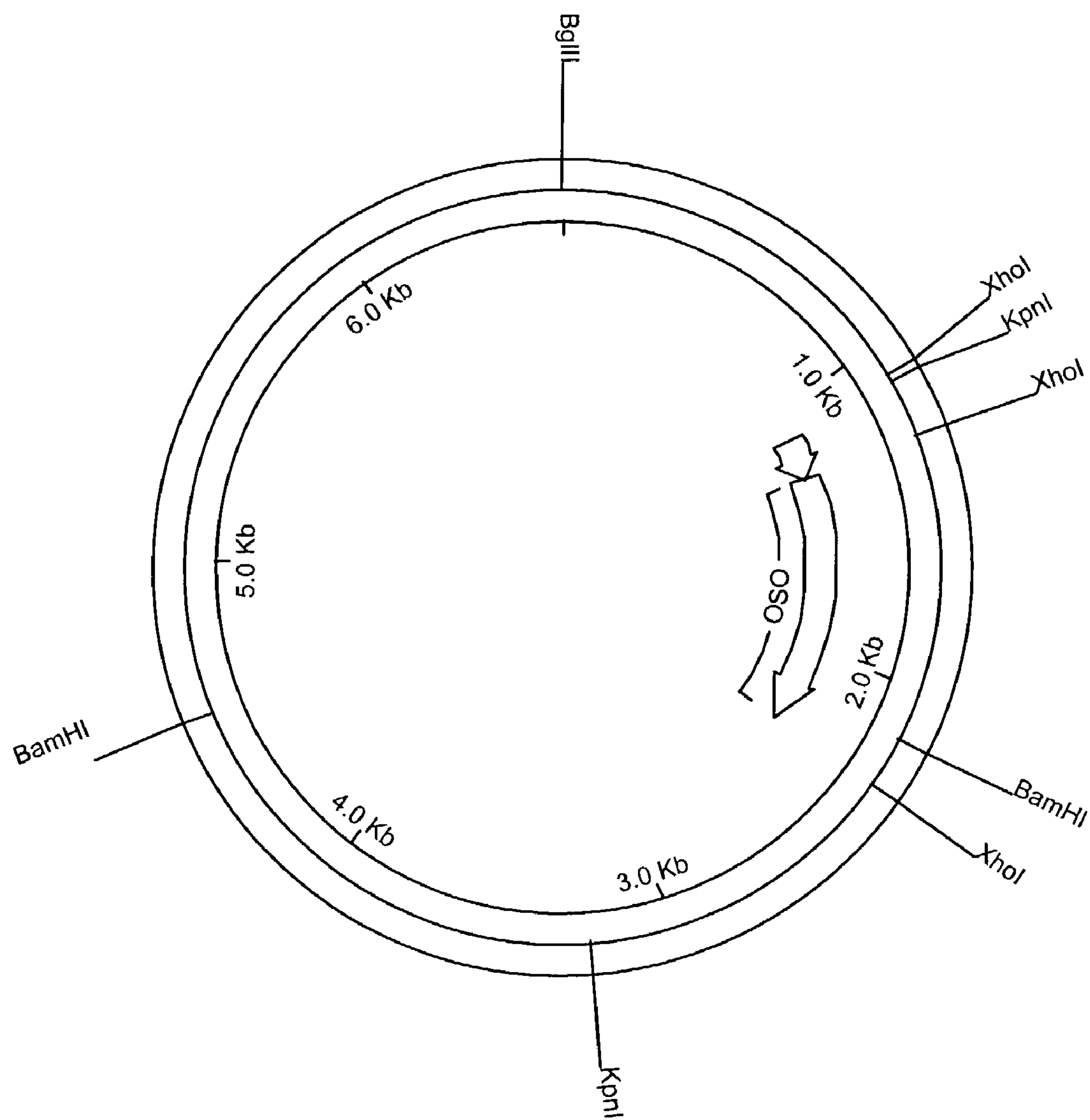
FIG. 5 is a diagram of the nucleic acid vector designated pRES-OSO.

The invention provides methods and materials related to expressing IgE polypeptides such as chimeric IgE polypeptides. Specifically, the invention provides nucleic acid vectors, host cells, and methods for producing chimeric IgE polypeptides.

Nucleic acid vectors can be designed to express chimeric IgE polypeptides. Such nucleic acid vectors can contain an insert sequence. The term "insert sequence" as used herein refers to a nucleic acid sequence that is inserted into a nucleic acid vector such that that inserted nucleic acid sequence can be expressed. Typically, an insert sequence is a nucleic acid sequence that encodes a chimeric IgE polypeptide. The term "chimeric IgE polypeptide" as used herein refers to a polypeptide having a combination of IgE domains from different species. A chimeric IgE polypeptide typically contains IgE constant heavy (CH) chain domains (e.g., CH1, CH2, CH3, or CH4). For example, an insert sequence having the sequence set forth in SEQ ID NO:2 can encode an opossum CH2-rat CH3-opossum CH4 (ORO) chimeric IgE polypeptide (SEQ ID NO:3). Other examples of insert sequences include, without limitation, an insert sequence having the sequence set forth in SEQ ID NO:5 that encodes an opossum CH2-human CH3-opossum CH4 (OSO) chimeric IgE polypeptide (SEQ ID NO:6), an insert sequence having the sequence set forth in SEQ ID NO:7 that encodes an opossum CH2-rat CH3-opossum CH2-rat CH3-opossum CH4 (ORORO) chimeric IgE polypeptide (SEQ ID NO:8), an insert sequence having the sequence set forth in SEQ ID NO:15 that encodes an opossum CH2-human CH3-opossum CH2-human CH3-opossum CH4 (OSOSO) chimeric IgE polypeptide (SEQ ID NO:16), as well as those chimeric IgE polypeptides disclosed in International Patent Application Serial No. PCT/SE99/01896. In addition to rat and human, IgE domains from other species may be used in chimeric insert sequences. Such species include, without limitation, dog, cat, horse, pig, cow, and monkey. For example, an insert sequence including IgE domains from opossum and monkey (e.g., cynomolgus) can encode an opossum CH2-cynomolgus CH3-opossum CH4 (OCO) chimeric IgE polypeptide. Other insert sequences having IgE domains from opossum and monkey include, without limitation, sequences that encode opossum CH2-cynomolgus CH3-opossum CH4 (OCO-H), where the sequence contains a C-terminal histidine-tag; sequences that encode opossum CH2-cynomolgus CH3-opossum CH2-cynomolgus CH3-opossum CH4 (OCOCO); and sequences that encode opossum CH2-cynomolgus CH3-opossum CH2-cynomolgus CH3-opossum CH4, where the sequence contains a C-terminal histidine-tag (OCOCO-H).

An insert sequence can be modified. Such modifications can include, without limitation, additions, deletions, substitutions, point mutations, and combinations thereof. An insert sequence can be modified to include a C-terminal polyhistidine sequence to aid in the purification of the polypeptide encoded by the insert sequence. Polyhistidine sequences used for this purpose have been described elsewhere (Ford et al., *Protein Expr. Purif.,* 2(2–3):95–107, 1991). For example, an insert sequence having the sequence set forth in SEQ ID NO:13 can encode an OSO chimeric IgE polypeptide including a C-terminal polyhistidine sequence (OSO-H; SEQ ID NO:14). An insert sequence can be modified to contain point mutations. For example, an insert sequence having the sequence set forth in SEQ ID NO:11 can encode an OSOSO chimeric IgE polypeptide containing point mutations in the human CH3 domains that abolish mast cell receptor binding (modOSOSO; SEQ ID NO:12). Other examples of modified insert sequences include, without limitation, an insert sequence having the sequence set forth in SEQ ID NO:17 that encodes an OSOSO chimeric IgE polypeptide including a C-terminal polyhistidine sequence (OSOSO-H; SEQ ID NO:18) and an insert sequence having the sequence set forth in SEQ ID NO:9 that encodes an OSOSO chimeric IgE polypeptide including a C-terminal polyhistidine sequence and containing point mutations in the human CH3 domains that abolish mast cell receptor binding (modOSOSO-H; SEQ ID NO:10).

A nucleic acid vector also can contain components that affect the expression of the insert sequence. Examples of such components include, without limitation, promoters, enhancers, leaders, and polyadenylation sequences. Such components can be operably linked to the insert sequence. The term "operably linked" as used herein refers to an arrangement where components so described are configured so as to perform their usual function. For example, a nucleic acid vector with an insert sequence encoding an OSOSO chimeric IgE polypeptide also can contain a cytomegalovirus (CMV) promoter (see, for example, Thomson et al., *Proc. Natl. Acad. Sci. U.S. A.,* 81(3):659–663, 1984), an immunoglobulin (Ig) leader sequence (see, for example, Neuberger et al., *EMBO J.,* 2(8):1373–1378, 1983), and a bovine growth hormone (bGH) polyadenylation sequence (see, for example, Goodwin et al., *J. Biol. Chem.,* 267: 16330–16334, 1992). In this case, the components are operably linked to the insert sequence such that the CMV promoter drives the expression of the insert sequence including the Ig leader sequence and bGH polyadenylation sequence, the Ig leader sequence directs the expressed insert sequence into the lumen of the endoplasmic reticulum in preparation for secretion, and the bGH polyadenylation sequence stabilizes the insert sequence transcript.

In addition, a nucleic acid vector can contain components that aid in the growth, maintenance, or selection of a host cell containing the nucleic acid vector. Such components include, without limitation, origins of replication and antibiotic selection markers. For example, a nucleic acid vector with a CMV promoter, an Ig leader sequence, an SV40 late polyadenylation sequence, and an insert sequence encoding an OSOSO chimeric IgE polypeptide can also contain an f1 origin of replication, a sequence that confers ampicillin resistance on a bacterial host cell when expressed, and a sequence that confers neomycin resistance on a mammalian host cell when expressed. Other examples of antibiotic selection markers include, without limitation, sequences that confer resistance to hygromycin B, puromycin, kanamycin, tetracycline, blasticidin S, Geneticin®, and zeocin on a host cell when expressed. Nucleic acid vectors that contain one or more than one component described herein can be obtained commercially from, for example, Invitrogen (Carlsbad, Calif.) and Promega (Madison, Wis.).

In one embodiment, the invention provides a nucleic acid vector (e.g., the pCI-neo vector from Promega, catalogue number E1841) containing at least one of the insert sequences provided herein (e.g., ORO, OSO, ORORO, modORORO-H, modOSOSO, OSO-H, OSOSO, and OSOSO-H). The invention also provides host cells that contain a nucleic acid vector described herein. Such cells can be prokaryotic cells (e.g., JM1O9 or DH5α) or eukaryotic cells (e.g., NS0, HeLa, BHK-21, COS-7, Sf9, or CHO). Host cells containing a nucleic acid vector provided herein may or may not express a polypeptide. For example, a host cell may function simply to propagate the nucleic acid vector for use in other host cells. In addition, the nucleic acid vector can be integrated into the genome of the host or maintained in an episomal state. Thus, a host cell can be stably or transiently transfected with a nucleic acid vector containing an insert sequence of the invention.

A host cell within the scope of the invention can contain a nucleic acid vector with an insert sequence that encodes a chimeric IgE polypeptide. For example, a host cell can contain a nucleic acid vector with an insert sequence encoding an OSO chimeric IgE polypeptide or any of the chimeric IgE polypeptides provided herein. In addition, a host cell can express the polypeptide encoded by the insert sequence.

Various methods can be used to introduce a nucleic acid vector into a host cell in vivo or in vitro. For example, calcium phosphate precipitation, electroporation, heat shock, lipofection, microinjection, and viral-mediated nucleic acid transfer are common methods that can be used to introduce a nucleic acid vector into a host cell. In addition, naked DNA can be delivered directly to cells in vivo as described elsewhere (U.S. Pat. Nos. 5,580,859 and 5,589,466 including continuations thereof). Further, a nucleic acid vector can be introduced into cells in the context of generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce a nucleic acid vector into animals to produce the founder lines of transgenic animals. Such techniques include, without limitation, pronuclear microinjection (U.S. Pat. No. 4,873,191); retrovirus mediated gene transfer into germ lines (Van der Putten et al., *Proc. Natl. Acad. Sci., USA,* 82:6148 (1985)); gene transfection into embryonic stem cells (Gossler A et al., *Proc Natl Acad Sci USA* 83:9065–9069 (1986)); gene targeting into embryonic stem cells (Thompson et al., *Cell,* 56:313 (1989)); nuclear transfer of somatic nuclei (Schnieke A E et al., *Science* 278:2130–2133 (1997)); and electroporation of embryos (Lo C W, *Mol. Cell. Biol.,* 3:1803–1814 (1983)). Once obtained, transgenic animals can be replicated using traditional breeding or animal cloning.

Various methods can be used to identify a host cell containing a nucleic acid vector of the invention. Such methods include, without limitation, PCR, nucleic acid hybridization techniques such as Northern and Southern analysis, and in situ nucleic acid hybridization. In some cases, immunohistochemistry and biochemical techniques can be used to determine if a cell contains a nucleic acid vector with a particular insert sequence by detecting the expression of a polypeptide encoded by that particular insert sequence.

The invention also provides methods for producing recombinant chimeric IgE polypeptides. Such methods involve culturing a host cell that expresses a chimeric IgE polypeptide and recovering the expressed chimeric IgE polypeptides. Any method can be used to recover a recombinant chimeric IgE polypeptide. For example, recombinant chimeric IgE polypeptides that are present in a host cell homogenate can be recovered using ion exchange chromatography. In another example, recombinant chimeric IgE polypeptides with polyhistidine sequences can be recovered from a host cell homogenate by passing the homogenate over a nickel column and eluating the polyhistidine-containing polypeptides with imidazole. A particular recombinant chimeric IgE polypeptide with a leader sequence that directs that polypeptide's secretion can be recovered from the growth medium of a host cell expressing that polypeptide. For example, the growth medium from a culture of mammalian host cells expressing and secreting ORO polypeptides can be collected, and the ORO polypeptides can be recovered using chromatography. It is understood that a leader sequence that directs the secretion of a polypeptide typically is removed from that polypeptide in the host cell by proteolysis. Thus, the recovered secreted polypeptide, in many cases, is free of any translated leader sequence.

In one embodiment, the cell medium from a clonal CHO cell line expressing and secreting ORO polypeptides is collected and centrifuged to remove cell debris. After centrifuging, the supernatant is dialyzed and passed over an ion exchange column allowing the ORO polypeptides to bind. The bound ORO polypeptides are eluted using a sodium chloride/sodium acetate gradient, and the eluated fractions are screened for recombinant ORO polypeptides using an ELISA technique. The eluated fractions with the best ELISA reactivity can be pooled and dialyzed again, and the dialyzed pooled fractions can be passed over a hydrophobic interaction column allowing the ORO polypeptides to bind. The bound ORO polypeptides are eluted using a sodium phosphate gradient, and the eluated fractions are again screened for recombinant ORO polypeptides using an ELISA technique. The eluated fractions with the best ELISA reactivity can be further analyzed by silver stained SDS-PAGE to estimate the purity of the ORO polypeptides.

The invention will be further described in the following examples, which do not limit the scope of the invention described in the claims.

EXAMPLES

Example 1

Nucleic Acid Vectors for Expressing Chimeric IgE Polypeptides

Plasmids containing cDNA sequences encoding polyhistidine-tagged ORO or OSO are used in PCRs with primers designed to amplify ORO or OSO without a polyhistidine tag (5'-AACTCGAGTACTTTATCTCTCCCAGAA-3' (SEQ ID NO:19) and 5'-ATCTCGAGATTAGTTACCAGCTGAGTAATGCA-3' (SEQ ID NO:20)). XhoI restriction enzyme recognition sites are included in each PCR primer to allow PCR amplification products to be ligated into an XhoI-digested and phosphatase-treated plasmid. Each PCR amplification cycle consists of a denaturing step at 94° C. for 30 seconds, an annealing step at 52° C. for 30 seconds, and an elongating step at 68° C. for 3 minutes. This amplification cycle was repeated 25 times. Each reaction begins with a single denaturing step at 94° C. for 2 minutes and ends with a single elongating step at 68° C. for 10 minutes. The resulting PCR amplification products are purified and digested with XhoI. The digested products are then purified. The resulting purified amplification products are ligated into an XhoI-digested and phosphatase-treated plasmid, producing ORO and OSO nucleic acid vectors. DNA sequencing and transient expression in CHO cells is used to verify the orientation, reading frame, and fidelity of each nucleic acid vector.

Example 2

Isolating Stable CHO Clones Expressing Chimeric IgE Polypeptides

The nucleic acid vectors described in Example 1 are linearized by digestion with PvuI. CHO cells are transfected with the linearized nucleic acid vectors using LipofectAMINE™ 2000 (Life Technologies, Rockville, Md.). After 24 hours, the transfected cells are seeded into three 96-well plates with selective medium consisting of DMEM containing 10% FBS and 600 μg/mL G418. After 21 days, clones are screened for recombinant chimeric IgE polypeptide expression by ELISA. Briefly, the wells of ELISA plates are coated with rabbit anti-OOO immunoglobulin diluted 1:5000 in coating buffer (0.1M sodium carbonate, pH 9.5). The coated plates are incubated overnight at 4° C. After washing the coated plates four times with PBS containing 0.05% Tween20, each well of the washed ELISA plates is treated with 100 μL of PBS containing 3% BSA for one hour at room temperature to block any subsequent non-specific binding interactions. After blocking, 100 μL of a recombinant IgE chimera protein sample is loaded into each well, and the loaded ELISA plate is incubated. Following the incubation, the plates are washed four times in PBS containing 0.05% Tween20. The washed plates are treated with 100 μL of either an HRP-conjugated goat anti human IgE antibody (KPL 074–1004, 1:2000; Merck Eurolab, Stockholm, Sweden) when detecting OSO (SEQ ID NO:6), or a monoclonal mouse anti-rat IgE antibody (MAS 314, Harlan Seralab, Leicestershire, England) when detecting ORO (SEQ ID NO:3), and then incubated for 1 hour at room temperature. Detecting ORO requires an additional incubation with an HRP-conjugated rabbit anti-mouse Ig antibody (P0260, Dako, Carpinteria, Calif.) for 1 hour at room temperature. Following the incubations, the treated plates are washed 8 times with PBS containing 0.05% Tween20 and developed according to the manufacturer's instructions. The protein concentrations are determined by measuring the absorbance at 490–650 nm.

Clones exhibiting the highest levels of recombinant chimeric IgE polypeptide expression for each nucleic acid vector are expanded and further selected by limiting dilution into 96-well plates. After selection, 48 clones are screened for recombinant chimeric IgE polypeptide expression by ELISA. Two clones exhibiting the highest levels of recombinant chimeric IgE polypeptide expression for each nucleic acid vector are expanded and further selected by limiting dilution into 96-well plates. After selection, the number of clones retaining the expression of recombinant chimeric IgE polypeptides after limiting dilution is determined by ELISA. One clone for each nucleic acid vector is expanded for large-scale recombinant chimeric IgE polypeptide production. A portion of the expanded clone is frozen and preserved as a stock. Clonal cell lines expressing ORO and OSO are generated in this manner.

Example 3

Purifying Recombinant Chimeric IgE Polypeptides

The clonal cell lines described in Example 2 are grown and maintained at 37° C., 5% $CO_2$ in cell medium. The cell medium containing secreted chimeric IgE polypeptides is collected every few days. The collected medium is centrifuged to remove cell debris. After centrifuging, the supernatant is dialyzed against 50 volumes of 25 mM sodium acetate buffer (pH 5.9) for 24 hours. The dialyzed supernatant is passed over a SP-Sepharose ion exchange column allowing the chimeric IgE polypeptides to bind. The bound chimeric IgE polypeptides are eluted in fractions using a gradient of 2 M sodium chloride in 25 mM sodium acetate buffer (pH 5.9). The eluated fractions are screened for recombinant chimeric IgE polypeptides by ELISA. The eluated fractions with the best ELISA reactivity are pooled and dialyzed against 10 mM sodium phosphate buffer containing 1.6 M ammonium sulphate (pH 6.5). The pooled fractions are passed over a phenyl- or butyl-Sepharose hydrophobic interaction column allowing the chimeric IgE polypeptides to bind. The bound chimeric IgE polypeptides are eluted in fractions using a gradient of 10 mM sodium phosphate buffer without ammonium sulphate (pH 6.5). The eluated fractions are screened for recombinant chimeric IgE polypeptides by ELISA. The eluated fractions with the best ELISA reactivity are further analyzed by silver stained SDS-PAGE to estimate the purity of the chimeric IgE polypeptides.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid vector consisting of the sequence set forth in SEQ ID NO:4.

2. An isolated host cell comprising a nucleic acid vector, wherein said nucleic acid vector comprises a cytomegalovirus promoter, an immunoglobulin (Ig) leader sequence, an insert sequence, and a SV40 late polyadenylation sequence, wherein said cytomegalovirus promoter is upstream from and operably linked to said insert sequence, said Ig leader sequence is downstream from said cytomegalovirus promoter and upstream from and operably linked to said insert sequence, said SV40 late polyadenylation sequence is downstream from and operably linked to said insert sequence, and said insert sequence encodes a chimeric IgE polypeptide, and wherein said insert sequence comprises a sequence selected from the group consisting of SEQ ID NO:2, SEQ ID NO:5, SEQ ID NO:7, SEQ ID NO:9, SEQ ID NO:11, SEQ ID NO:13, SEQ ID NO:15, and SEQ ID NO:17.

3. An isolated host cell comprising a nucleic acid vector, wherein said nucleic acid vector comprises a cytomegalovirus promoter, an Ig leader sequence, an insert sequence, and a SV40 late polyadenylation sequence, wherein said cytomegalovirus promoter is upstream from and operably linked to said insert sequence, said Ig leader sequence is downstream from said cytomegalovirus promoter and upstream from and operably linked to said insert sequence, said SV40 late polyadenylation sequence is downstream from and operably linked to said insert sequence, and said insert sequence encodes a chimeric IgE polypeptide, and wherein said chimeric IgE polypeptide encoded by said insert sequence comprises a sequence selected from the group consisting of SEQ ID NO:3, SEQ ID NO:6, SEQ ID NO:8, SEQ ID NO:10, SEQ ID NO:12, SEQ ID NO:14, SEQ ID NO:16, and SEQ ID NO:18.

4. A method for producing a chimeric IgE polypeptide, said method comprising:

(a) culturing a eukaryotic cell comprising a vector comprising a cytomegalovirus promoter, an Ig leader sequence, an insert sequence, and a SV40 late polyadenylation sequence, wherein said cytomegalovirus promoter is upstream from and operably linked to said insert sequence, said Ig leader sequence is downstream from said cytomegalovirus promoter and upstream from and operably linked to said insert sequence, said SV40 late polyadenylation sequence is downstream from and operably linked to said insert sequence, and said insert sequence encodes a chimeric IgE polypeptide, and wherein said insert sequence comprises a sequence selected from the group consisting of SEQ ID NO:2, SEQ ID NO:5, SEQ ID NO:7, SEQ ID NO:9, SEQ ID NO:11, SEQ ID NO:13, SEQ ID NO:15, and SEQ ID NO:17; and (b) recovering said chimeric IgE polypeptide from said culture.

5. A method for producing a chimeric IgE polypeptide, said method comprising:

(a) culturing a eukaryotic cell comprising a vector comprising a cytomegalovirus promoter, an Ig leader sequence, an insert sequence, and a SV40 late polyadenylation sequence, wherein said cytomegalovirus promoter is upstream from and operably linked to said insert sequence, said Ig leader sequence is downstream from said cytomegalovirus promoter and upstream from and operably linked to said insert sequence, said SV40 late polyadenylation sequence is downstream from and operably linked to said insert sequence, and said insert sequence encodes a chimeric IgE polypeptide, and wherein said chimeric IgE polypeptide comprises a sequence selected from the group consisting of SEQ ID NO:3, SEQ ID NO:6, SEQ ID NO:8, SEQ ID NO:10, SEQ ID NO:12, SEQ ID NO:14, SEQ ID NO:16, and SEQ ID NO:18; and (b recovering said chimeric IgE polypeptide from said culture.

6. The host cell of claim 2, wherein said insert sequence comprises a sequence selected from the group consisting of SEQ ID NO:2, SEQ ID NO:5, SEQ ID NO:7, SEQ ID NO:11, and SEQ ID NO:15.

7. The host cell of claim 2, wherein said host cell is a JM109, DH5α, NS0, HeLa, BHK-21, COS-7, Sf9, or CHO cell.

8. The host cell of claim 2, wherein said host cell is a CHO cell.

9. The host cell of claim 3, wherein said chimeric IgE polypeptide encoded by said insert sequence comprises a sequence selected from the group consisting of SEQ ID NO:3, SEQ ID NO:6, SEQ ID NO:8, SEQ ID NO:12, and SEQ ID NO:16.

10. The host cell of claim 3, wherein said host cell is a JM109, DH5α, NS0, HeLa, BHK-21, COS-7, Sf9, or CHO cell.

11. The host cell of claim 3, wherein said host cell is a CHO cell.

12. The method of claim 3, wherein said insert sequence comprises a sequence selected from the group consisting of SEQ ID NO:2, SEQ ID NO:5, SEQ ID NO:7, SEQ ID NO:11, and SEQ ID NO:15.

13. The method of claim 4, wherein said cell is a NS0, HeLa, BHK-21, COS-7, Sf9, or CHO cell.

14. The method of claim 4, wherein said cell is a CHO cell.

15. The method of claim 5, wherein said chimeric IgE polypeptide encoded by said insert sequence comprises a sequence selected from the group consisting of SEQ ID NO:3, SEQ ID NO:6, SEQ ID NO:8, SEQ ID NO:12, and SEQ ID NO:16.

16. The method of claim 5, wherein said cell is a NS0, HeLa, BHK-21, COS-7, Sf9, or CHO cell.

17. The method of claim 5, wherein said cell is a CHO cell.

* * * * *

UNITED STATES PATENT AND TRADEMARK OFFICE

CERTIFICATE OF CORRECTION

PATENT NO. : 7,232,898 B2
APPLICATION NO. : 10/438794
DATED : June 19, 2007
INVENTOR(S) : Mats Lundgren, Alexis Fuentes and Ann-Christin Magnusson It is certified that error appears in the above-identified patent and that said Letters Patent is hereby corrected as shown below:

Column 54, line 66 (Claim 12), please delete “3” and insert --4-- therefor.

Signed and Sealed this

Twenty-sixth Day of August, 2008

JON W. DUDAS
*Director of the United States Patent and Trademark Office*

SEQUENCE LISTING

```
<160> NUMBER OF SEQ ID NOS: 20

<210> SEQ ID NO 1
<211> LENGTH: 6649
<212> TYPE: DNA
<213> ORGANISM: Artificial Sequence
<220> FEATURE:
<223> OTHER INFORMATION: Vector designated pRES-ORO
```

-continued

<400> SEQUENCE: 1

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cacgcgtggt acctctagag tcgaccccgg gccgacctca   1140
ccatgggatg gagctgtatc atcctcttct tggtagcaac agctacaggt aaggggctca   1200
cagtagcagg cttgaggtct ggacatatat atgggtgaca atgacatcca ctttgccttt   1260
ctctccacag gtgtgcattc ctcgagtact ttatctctcc cagaaagtgg ccctgtgaca   1320
atcatcccac ctacagtgaa gctcttccac tcatcctgtg acccccgagg ggatgctcat   1380
tccaccatcc agctgctctg ccttgtctct ggcttctccc cagccaaggt ccatgtgacc   1440
tggctggtag atggacagga ggctgaaaat ctctttccct atacaaccag acctaagagg   1500
gaagggggac agacttttc tctacaaagt gaagtcaaca tcacacaggg ccagtggatg   1560
tcatcaaaca cctacacctg ccatgtcaag cacaatggca gcatctttga agacagttct   1620
agaagatgct cagatgatga gccccggggt gtgattacct acctgatccc acccagtccc   1680
ctcgacctgt atgaaaatgg gactcccaaa cttacctgtc tggttttgga cctggaaagt   1740
gaggagaata tcaccgtgac gtgggtccga gagcgtaaga agtctatagg ttcggcatcc   1800
cagaggagta ccaagcacca taatgccaca accagtatca cctccatctt gccagtggat   1860
gccaaggact ggatcgaagg tgaaggctac cagtgcagag tggaccaccc tcactttccc   1920
aagcccattg tgcgttccat caccaagctt gctagcccag gcaaacgctt agcccccgag   1980
gtatatatgc tccctccatc tccagaggaa acaggaacca ctcgcactgt aacctgccta   2040
attcggggtt tctacccttc tgaaatatct gtccaatggc tgtttaataa cgaagaggac   2100
cacactggac accatactac cacccgtccc caaaaggacc acggaacgga tccttccttc   2160
ttcctctaca gccgaatgct tgtcaacaag tctatttggg aaaaaggcaa tctcgtcacc   2220
tgccgtgtgg tgcatgaagc cctacctggc tcccgcaccc tggaaaaaag cctgcattac   2280
tcagctggta actaatctcg agcagggcgg ccgcttccct ttagtgaggg ttaatgcttc   2340
```

-continued

```
gagcagacat gataagatac attgatgagt ttggacaaac cacaactaga atgcagtgaa   2400
aaaaatgctt tatttgtgaa atttgtgatg ctattgcttt atttgtaacc attataagct   2460
gcaataaaca agttaacaac aacaattgca ttcattttat gtttcaggtt caggggaga    2520
tgtgggaggt tttttaaagc aagtaaaacc tctacaaatg tggtaaaatc cgataaggat   2580
cgatccgggc tggcgtaata gcgaagaggc ccgcaccgat cgcccttccc aacagttgcg   2640
cagcctgaat ggcgaatgga cgcgccctgt agcggcgcat taagcgcggc gggtgtggtg   2700
gttacgcgca gcgtgaccgc tacacttgcc agcgccctag cgcccgctcc tttcgctttc   2760
ttcccttcct ttctcgccac gttcgccggc tttccccgtc aagctctaaa tcgggggctc   2820
cctttagggt tccgatttag tgctttacgg cacctcgacc ccaaaaaact tgattagggt   2880
gatggttcac gtagtgggcc atcgccctga tagacggttt ttcgcccttt gacgttggag   2940
tccacgttct ttaatagtgg actcttgttc caaactggaa caacactcaa ccctatctcg   3000
gtctattctt ttgatttata agggattttg ccgatttcgg cctattggtt aaaaaatgag   3060
ctgatttaac aaaaatttaa cgcgaatttt aacaaaatat taacgcttac aatttcctga   3120
tgcggtattt tctccttacg catctgtgcg gtatttcaca ccgcatacgc ggatctgcgc   3180
agcaccatgg cctgaaataa cctctgaaag aggaacttgg ttaggtacct tctgaggcgg   3240
aaagaaccag ctgtggaatg tgtgtcagtt agggtgtgga aagtccccag gctccccagc   3300
aggcagaagt atgcaaagca tgcatctcaa ttagtcagca accaggtgtg gaaagtcccc   3360
aggctcccca gcaggcagaa gtatgcaaag catgcatctc aattagtcag caaccatagt   3420
cccgccccta actccgccca tcccgcccct aactccgccc agttccgccc attctccgcc   3480
ccatggctga ctaatttttt ttatttatgc agaggccgag gccgcctcgg cctctgagct   3540
attccagaag tagtgaggag gcttttttgg aggcctaggc ttttgcaaaa agcttgattc   3600
ttctgacaca acagtctcga acttaaggct agagccacca tgattgaaca agatggattg   3660
cacgcaggtt ctccggccgc ttgggtggag aggctattcg gctatgactg ggcacaacag   3720
acaatcggct gctctgatgc cgccgtgttc cggctgtcag cgcaggggcg cccggttctt   3780
tttgtcaaga ccgacctgtc cggtgccctg aatgaactgc aggacgaggc agcgcggcta   3840
tcgtggctgg ccacgacggg cgttccttgc gcagctgtgc tcgacgttgt cactgaagcg   3900
ggaagggact ggctgctatt gggcgaagtg ccggggcagg atctcctgtc atctcacctt   3960
gctcctgccg agaaagtatc catcatggct gatgcaatgc ggcggctgca tacgcttgat   4020
ccggctacct gcccattcga ccaccaagcg aaacatcgca tcgagcgagc acgtactcgg   4080
atggaagccg gtcttgtcga tcaggatgat ctggacgaag agcatcaggg gctcgcgcca   4140
gccgaactgt tcgccaggct caaggcgcgc atgcccgacg gcgaggatct cgtcgtgacc   4200
catggcgatg cctgcttgcc gaatatcatg gtggaaaatg gccgcttttc tggattcatc   4260
gactgtggcc ggctgggtgt ggcggaccgc tatcaggaca tagcgttggc tacccgtgat   4320
attgctgaag agcttggcgg cgaatgggct gaccgcttcc tcgtgcttta cggtatcgcc   4380
gctcccgatt cgcagcgcat cgccttctat cgccttcttg acgagttctt ctgagcggga   4440
ctctggggtt cgaaatgacc gaccaagcga cgcccaacct gccatcacga tggccgcaat   4500
aaaatatctt tattttcatt acatctgtgt gttggttttt tgtgtgaatc gatagcgata   4560
aggatccgcg tatggtgcac tctcagtaca atctgctctg atgccgcata gttaagccag   4620
ccccgacacc cgccaacacc cgctgacgcg ccctgacggg cttgtctgct cccggcatcc   4680
```

-continued

```
gcttacagac aagctgtgac cgtctccggg agctgcatgt gtcagaggtt ttcaccgtca   4740

tcaccgaaac gcgcgagacg aaagggcctc gtgatacgcc tatttttata ggttaatgtc   4800

atgataataa tggtttctta gacgtcaggt ggcacttttc ggggaaatgt gcgcggaacc   4860

cctatttgtt tatttttcta aatacattca aatatgtatc cgctcatgag acaataaccc   4920

tgataaatgc ttcaataata ttgaaaaagg aagagtatga gtattcaaca tttccgtgtc   4980

gcccttattc ccttttttgc ggcattttgc cttcctgttt ttgctcaccc agaaacgctg   5040

gtgaaagtaa aagatgctga agatcagttg ggtgcacgag tgggttacat cgaactggat   5100

ctcaacagcg gtaagatcct tgagagtttt cgccccgaag aacgttttcc aatgatgagc   5160

acttttaaag ttctgctatg tggcgcggta ttatcccgta ttgacgccgg gcaagagcaa   5220

ctcggtcgcc gcatacacta ttctcagaat gacttggttg agtactcacc agtcacagaa   5280

aagcatctta cggatggcat gacagtaaga gaattatgca gtgctgccat aaccatgagt   5340

gataacactg cggccaactt acttctgaca acgatcggag gaccgaagga gctaaccgct   5400

tttttgcaca acatggggga tcatgtaact cgccttgatc gttgggaacc ggagctgaat   5460

gaagccatac caaacgacga gcgtgacacc acgatgcctg tagcaatggc aacaacgttg   5520

cgcaaactat taactggcga actacttact ctagcttccc ggcaacaatt aatagactgg   5580

atggaggcgg ataaagttgc aggaccactt ctgcgctcgg cccttccggc tggctggttt   5640

attgctgata aatctggagc cggtgagcgt gggtctcgcg gtatcattgc agcactgggg   5700

ccagatggta agccctcccg tatcgtagtt atctacacga cggggagtca ggcaactatg   5760

gatgaacgaa atagacagat cgctgagata ggtgcctcac tgattaagca ttggtaactg   5820

tcagaccaag tttactcata tatactttag attgatttaa aacttcattt ttaatttaaa   5880

aggatctagg tgaagatcct ttttgataat ctcatgacca aaatccctta acgtgagttt   5940

tcgttccact gagcgtcaga ccccgtagaa aagatcaaag gatcttcttg agatcctttt   6000

tttctgcgcg taatctgctg cttgcaaaca aaaaaaccac cgctaccagc ggtggtttgt   6060

ttgccggatc aagagctacc aactcttttt ccgaaggtaa ctggcttcag cagagcgcag   6120

ataccaaata ctgttcttct agtgtagccg tagttaggcc accacttcaa gaactctgta   6180

gcaccgccta catacctcgc tctgctaatc ctgttaccag tggctgctgc cagtggcgat   6240

aagtcgtgtc ttaccgggtt ggactcaaga cgatagttac cggataaggc gcagcggtcg   6300

ggctgaacgg ggggttcgtg cacacagccc agcttggagc gaacgaccta caccgaactg   6360

agatacctac agcgtgagct atgagaaagc gccacgcttc ccgaagggag aaaggcggac   6420

aggtatccgg taagcggcag ggtcggaaca ggagagcgca cgagggagct tccaggggga   6480

aacgcctggt atctttatag tcctgtcggg tttcgccacc tctgacttga gcgtcgattt   6540

ttgtgatgct cgtcaggggg gcggagccta tggaaaaacg ccagcaacgc ggccttttta   6600

cggttcctgg ccttttgctg gccttttgct cacatggctc gacagatct               6649
```

<210> SEQ ID NO 2
<211> LENGTH: 1011
<212> TYPE: DNA
<213> ORGANISM: Artificial Sequence
<220> FEATURE:
<223> OTHER INFORMATION: Insert sequence designated ORO

<400> SEQUENCE: 2

```
tcgagtactt tatctctccc agaaagtggc cctgtgacaa tcatcccacc tacagtgaag     60

ctcttccact catcctgtga cccccgaggg gatgctcatt ccaccatcca gctgctctgc    120
```

```
cttgtctctg gcttctcccc agccaaggtc catgtgacct ggctggtaga tggacaggag    180

gctgaaaatc tctttcccta tacaaccaga cctaagaggg aagggggaca gactttttct    240

ctacaaagtg aagtcaacat cacacagggc cagtggatgt catcaaacac ctacacctgc    300

catgtcaagc acaatggcag catctttgaa gacagttcta gaagatgctc agatgatgag    360

ccccggggtg tgattaccta cctgatccca cccagtcccc tcgacctgta tgaaaatggg    420

actcccaaac ttacctgtct ggttttggac ctggaaagtg aggagaatat caccgtgacg    480

tgggtccgag agcgtaagaa gtctataggt tcggcatccc agaggagtac caagcaccat    540

aatgccacaa ccagtatcac ctccatcttg ccagtggatg ccaaggactg gatcgaaggt    600

gaaggctacc agtgcagagt ggaccaccct cactttccca agcccattgt gcgttccatc    660

accaagcttg ctagcccagg caaacgctta gcccccgagg tatatatgct ccctccatct    720

ccagaggaaa caggaaccac tcgcactgta acctgcctaa ttcggggttt ctacccttct    780

gaaatatctg tccaatggct gtttaataac gaagaggacc acactggaca ccatactacc    840

acccgtcccc aaaaggacca cggaacggat ccttccttct tcctctacag ccgaatgctt    900

gtcaacaagt ctatttggga aaaaggcaat ctcgtcacct gccgtgtggt gcatgaagcc    960

ctacctggct cccgcaccct ggaaaaaagc ctgcattact cagctggtaa c            1011
```

<210> SEQ ID NO 3
<211> LENGTH: 337
<212> TYPE: PRT
<213> ORGANISM: Artificial Sequence
<220> FEATURE:
<223> OTHER INFORMATION: Synthetic polypeptide designated ORO

<400> SEQUENCE: 3

```
Ser Ser Thr Leu Ser Leu Pro Glu Ser Gly Pro Val Thr Ile Ile Pro
 1               5                  10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Arg Cys Ser Asp Asp Glu Pro Arg Gly Val Ile Thr Tyr Leu
        115                 120                 125

Ile Pro Pro Ser Pro Leu Asp Leu Tyr Glu Asn Gly Thr Pro Lys Leu
    130                 135                 140

Thr Cys Leu Val Leu Asp Leu Glu Ser Glu Glu Asn Ile Thr Val Thr
145                 150                 155                 160

Trp Val Arg Glu Arg Lys Lys Ser Ile Gly Ser Ala Ser Gln Arg Ser
                165                 170                 175

Thr Lys His His Asn Ala Thr Thr Ser Ile Thr Ser Ile Leu Pro Val
            180                 185                 190

Asp Ala Lys Asp Trp Ile Glu Gly Glu Gly Tyr Gln Cys Arg Val Asp
        195                 200                 205
```

-continued

```
His Pro His Phe Pro Lys Pro Ile Val Arg Ser Ile Thr Lys Leu Ala
    210                 215                 220

Ser Pro Gly Lys Arg Leu Ala Pro Glu Val Tyr Met Leu Pro Pro Ser
225                 230                 235                 240

Pro Glu Glu Thr Gly Thr Thr Arg Thr Val Thr Cys Leu Ile Arg Gly
                245                 250                 255

Phe Tyr Pro Ser Glu Ile Ser Val Gln Trp Leu Phe Asn Asn Glu Glu
            260                 265                 270

Asp His Thr Gly His His Thr Thr Thr Arg Pro Gln Lys Asp His Gly
        275                 280                 285

Thr Asp Pro Ser Phe Phe Leu Tyr Ser Arg Met Leu Val Asn Lys Ser
    290                 295                 300

Ile Trp Glu Lys Gly Asn Leu Val Thr Cys Arg Val Val His Glu Ala
305                 310                 315                 320

Leu Pro Gly Ser Arg Thr Leu Glu Lys Ser Leu His Tyr Ser Ala Gly
                325                 330                 335

Asn


<210> SEQ ID NO 4
<211> LENGTH: 6652
<212> TYPE: DNA
<213> ORGANISM: Artificial Sequence
<220> FEATURE:
<223> OTHER INFORMATION: Vector designated pRES-OSO

<400> SEQUENCE: 4

tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaacaactg    660

cgatcgcccg ccccgttgac gcaaatgggc ggtaggcgtg tacggtggga ggtctatata    720

agcagagctc gtttagtgaa ccgtcagatc actagaagct ttattgcggt agtttatcac    780

agttaaattg ctaacgcagt cagtgcttct gacacaacag tctcgaactt aagctgcagt    840

gactctctta aggtagcctt gcagaagttg gtcgtgaggc actgggcagg taagtatcaa    900

ggttacaaga caggtttaag gagaccaata gaaactgggc ttgtcgagac agagaagact    960

cttgcgtttc tgataggcac ctattggtct tactgacatc cactttgcct ttctctccac   1020

aggtgtccac tcccagttca attacagctc ttaaggctag agtacttaat acgactcact   1080

ataggctagc ctcgagaatt cacgcgtggt acctctagag tcgaccccgg gccgacctca   1140

ccatgggatg gagctgtatc atcctcttct tggtagcaac agctacaggt aaggggctca   1200

cagtagcagg cttgaggtct ggacatatat atgggtgaca atgacatcca ctttgccttt   1260
```

-continued

```
ctctccacag gtgtgcattc ctcgagtact ttatctctcc cagaaagtgg ccctgtgaca   1320
atcatcccac ctacagtgaa gctcttccac tcatcctgtg acccccgagg ggatgctcat   1380
tccaccatcc agctgctctg ccttgtctct ggcttctccc cagccaaggt ccatgtgacc   1440
tggctggtag atggacagga ggctgaaaat ctctttccct atacaaccag acctaagagg   1500
gaagggggac agactttttc tctacaaagt gaagtcaaca tcacacaggg ccagtggatg   1560
tcatcaaaca cctacacctg ccatgtcaag cacaatggca gcatctttga agacagttct   1620
agaaagtgtg cagattccaa cccgagaggg gtgagcgcct acctaagccg gcccagcccg   1680
ttcgacctgt tcatccgcaa gtcgcccacg atcacctgtc tggtggtgga cctggcaccc   1740
agcaagggga ccgtgaacct gacctggtcc cgggccagtg ggaagcctgt gaaccactcc   1800
accagaaagg aggagaagca gcgcaatggc acgttaaccg tcacgtccac cctgccggtg   1860
ggcacccgag actggatcga gggggagacc taccagtgca gggtgaccca cccccacctg   1920
cccagggccc tcatgcggtc cacgaccaag cttgctagcc caggcaaacg cttagccccc   1980
gaggtatata tgctccctcc atctccagag gaaacaggaa ccactcgcac tgtaacctgc   2040
ctaattcggg gtttctaccc ttctgaaata tctgtccaat ggctgtttaa taacgaagag   2100
gaccacactg gacaccatac taccacccgt ccccaaaagg accacggaac ggatccttcc   2160
ttcttcctct acagccgaat gcttgtcaac aagtctattt gggaaaaagg caatctcgtc   2220
acctgccgtg tggtgcatga agccctacct ggctcccgca ccctggaaaa aagcctgcat   2280
tactcagctg gtaactaatc tcgagcaggg cggccgcttc cctttagtga gggttaatgc   2340
ttcgagcaga catgataaga tacattgatg agtttggaca aaccacaact agaatgcagt   2400
gaaaaaaatg ctttatttgt gaaatttgtg atgctattgc tttatttgta accattataa   2460
gctgcaataa acaagttaac aacaacaatt gcattcattt tatgtttcag gttcaggggg   2520
agatgtggga ggttttttaa agcaagtaaa acctctacaa atgtggtaaa atccgataag   2580
gatcgatccg ggctggcgta atagcgaaga ggcccgcacc gatcgccctt cccaacagtt   2640
gcgcagcctg aatggcgaat ggacgcgccc tgtagcggcg cattaagcgc ggcgggtgtg   2700
gtggttacgc gcagcgtgac cgctacactt gccagcgccc tagcgcccgc tcctttcgct   2760
ttcttccctt cctttctcgc cacgttcgcc ggctttcccc gtcaagctct aaatcggggg   2820
ctccctttag ggttccgatt tagtgcttta cggcacctcg accccaaaaa acttgattag   2880
ggtgatggtt cacgtagtgg gccatcgccc tgatagacgg tttttcgccc tttgacgttg   2940
gagtccacgt tctttaatag tggactcttg ttccaaactg gaacaacact caaccctatc   3000
tcggtctatt cttttgattt ataagggatt ttgccgattt cggcctattg gttaaaaaat   3060
gagctgattt aacaaaaatt taacgcgaat tttaacaaaa tattaacgct tacaatttcc   3120
tgatgcggta ttttctcctt acgcatctgt gcggtatttc acaccgcata cgcggatctg   3180
cgcagcacca tggcctgaaa taacctctga aagaggaact tggttaggta ccttctgagg   3240
cggaaagaac cagctgtgga atgtgtgtca gttagggtgt ggaaagtccc caggctcccc   3300
agcaggcaga agtatgcaaa gcatgcatct caattagtca gcaaccaggt gtggaaagtc   3360
cccaggctcc ccagcaggca gaagtatgca aagcatgcat ctcaattagt cagcaaccat   3420
agtcccgccc ctaactccgc ccatcccgcc cctaactccg cccagttccg cccattctcc   3480
gccccatggc tgactaattt tttttattta tgcagaggcc gaggccgcct cggcctctga   3540
gctattccag aagtagtgag gaggcttttt tggaggccta ggcttttgca aaaagcttga   3600
ttcttctgac acaacagtct cgaacttaag gctagagcca ccatgattga acaagatgga   3660
```

-continued

```
ttgcacgcag gttctccggc cgcttgggtg gagaggctat tcggctatga ctgggcacaa   3720
cagacaatcg gctgctctga tgccgccgtg ttccggctgt cagcgcaggg gcgcccggtt   3780
ctttttgtca agaccgacct gtccggtgcc ctgaatgaac tgcaggacga ggcagcgcgg   3840
ctatcgtggc tggccacgac gggcgttcct tgcgcagctg tgctcgacgt tgtcactgaa   3900
gcgggaaggg actggctgct attgggcgaa gtgccggggc aggatctcct gtcatctcac   3960
cttgctcctg ccgagaaagt atccatcatg gctgatgcaa tgcggcggct gcatacgctt   4020
gatccggcta cctgcccatt cgaccaccaa gcgaaacatc gcatcgagcg agcacgtact   4080
cggatggaag ccggtcttgt cgatcaggat gatctggacg aagagcatca ggggctcgcg   4140
ccagccgaac tgttcgccag gctcaaggcg cgcatgcccg acggcgagga tctcgtcgtg   4200
acccatggcg atgcctgctt gccgaatatc atggtggaaa atggccgctt ttctggattc   4260
atcgactgtg gccggctggg tgtggcggac cgctatcagg acatagcgtt ggctacccgt   4320
gatattgctg aagagcttgg cggcgaatgg gctgaccgct tcctcgtgct ttacggtatc   4380
gccgctcccg attcgcagcg catcgccttc tatcgccttc ttgacgagtt cttctgagcg   4440
ggactctggg gttcgaaatg accgaccaag cgacgcccaa cctgccatca cgatggccgc   4500
aataaaatat ctttattttc attacatctg tgtgttggtt ttttgtgtga atcgatagcg   4560
ataaggatcc gcgtatggtg cactctcagt acaatctgct ctgatgccgc atagttaagc   4620
cagccccgac acccgccaac acccgctgac gcgccctgac gggcttgtct gctcccggca   4680
tccgcttaca gacaagctgt gaccgtctcc gggagctgca tgtgtcagag gttttcaccg   4740
tcatcaccga aacgcgcgag acgaaagggc ctcgtgatac gcctattttt ataggttaat   4800
gtcatgataa taatggtttc ttagacgtca ggtggcactt ttcggggaaa tgtgcgcgga   4860
acccctattt gtttattttt ctaaatacat tcaaatatgt atccgctcat gagacaataa   4920
ccctgataaa tgcttcaata atattgaaaa aggaagagta tgagtattca acatttccgt   4980
gtcgccctta ttcccttttt tgcggcattt tgccttcctg tttttgctca cccagaaacg   5040
ctggtgaaag taaaagatgc tgaagatcag ttgggtgcac gagtgggtta catcgaactg   5100
gatctcaaca gcggtaagat ccttgagagt tttcgccccg aagaacgttt tccaatgatg   5160
agcactttta aagttctgct atgtggcgcg gtattatccc gtattgacgc cgggcaagag   5220
caactcggtc gccgcataca ctattctcag aatgacttgg ttgagtactc accagtcaca   5280
gaaaagcatc ttacggatgg catgacagta agagaattat gcagtgctgc cataaccatg   5340
agtgataaca ctgcggccaa cttacttctg acaacgatcg gaggaccgaa ggagctaacc   5400
gcttttttgc acaacatggg ggatcatgta actcgccttg atcgttggga accggagctg   5460
aatgaagcca taccaaacga cgagcgtgac accacgatgc ctgtagcaat ggcaacaacg   5520
ttgcgcaaac tattaactgg cgaactactt actctagctt cccggcaaca attaatagac   5580
tggatggagg cggataaagt tgcaggacca cttctgcgct cggcccttcc ggctggctgg   5640
tttattgctg ataaatctgg agccggtgag cgtgggtctc gcggtatcat tgcagcactg   5700
gggccagatg gtaagccctc ccgtatcgta gttatctaca cgacggggag tcaggcaact   5760
atggatgaac gaaatagaca gatcgctgag ataggtgcct cactgattaa gcattggtaa   5820
ctgtcagacc aagtttactc atatatactt tagattgatt taaaacttca tttttaattt   5880
aaaaggatct aggtgaagat cctttttgat aatctcatga ccaaaatccc ttaacgtgag   5940
ttttcgttcc actgagcgtc agaccccgta gaaaagatca aaggatcttc ttgagatcct   6000
```

-continued

```
tttttctgc gcgtaatctg ctgcttgcaa acaaaaaaac caccgctacc agcggtggtt   6060

tgtttgccgg atcaagagct accaactctt tttccgaagg taactggctt cagcagagcg   6120

cagataccaa atactgttct tctagtgtag ccgtagttag gccaccactt caagaactct   6180

gtagcaccgc ctacatacct cgctctgcta atcctgttac cagtggctgc tgccagtggc   6240

gataagtcgt gtcttaccgg gttggactca agacgatagt taccggataa ggcgcagcgg   6300

tcgggctgaa cggggggttc gtgcacacag cccagcttgg agcgaacgac ctacaccgaa   6360

ctgagatacc tacagcgtga gctatgagaa agcgccacgc ttcccgaagg gagaaaggcg   6420

gacaggtatc cggtaagcgg cagggtcgga acaggagagc gcacgaggga gcttccaggg   6480

ggaaacgcct ggtatcttta tagtcctgtc gggtttcgcc acctctgact tgagcgtcga   6540

tttttgtgat gctcgtcagg ggggcggagc ctatggaaaa acgccagcaa cgcggccttt   6600

ttacggttcc tggccttttg ctggcctttt gctcacatgg ctcgacagat ct           6652
```

```
<210> SEQ ID NO 5
<211> LENGTH: 1014
<212> TYPE: DNA
<213> ORGANISM: Artificial Sequence
<220> FEATURE:
<223> OTHER INFORMATION: Insert sequence designated OSO

<400> SEQUENCE: 5

tcgagtactt tatctctccc agaaagtggc cctgtgacaa tcatcccacc tacagtgaag     60

ctcttccact catcctgtga cccccgaggg gatgctcatt ccaccatcca gctgctctgc    120

cttgtctctg gcttctcccc agccaaggtc catgtgacct ggctggtaga tggacaggag    180

gctgaaaatc tctttcccta tacaaccaga cctaagaggg aaggggggaca gactttttct    240

ctacaaagtg aagtcaacat cacacagggc cagtggatgt catcaaacac ctacacctgc    300

catgtcaagc acaatggcag catctttgaa gacagttcta gaaagtgtgc agattccaac    360

ccgagagggg tgagcgccta cctaagccgg cccagcccgt tcgacctgtt catccgcaag    420

tcgcccacga tcacctgtct ggtggtggac ctggcaccca gcaaggggac cgtgaacctg    480

acctggtccc gggccagtgg gaagcctgtg aaccactcca ccagaaagga ggagaagcag    540

cgcaatggca cgttaaccgt cacgtccacc ctgccggtgg gcacccgaga ctggatcgag    600

ggggagacct accagtgcag ggtgacccac ccccacctgc ccagggccct catgcggtcc    660

acgaccaagc ttgctagccc aggcaaacgc ttagcccccg aggtatatat gctccctcca    720

tctccagagg aaacaggaac cactcgcact gtaacctgcc taattcgggg tttctaccct    780

tctgaaatat ctgtccaatg gctgtttaat aacgaagagg accacactgg acaccatact    840

accacccgtc cccaaaagga ccacggaacg gatccttcct tcttcctcta cagccgaatg    900

cttgtcaaca agtctatttg ggaaaaaggc aatctcgtca cctgccgtgt ggtgcatgaa    960

gccctacctg gctcccgcac cctggaaaaa agcctgcatt actcagctgg taac         1014
```

```
<210> SEQ ID NO 6
<211> LENGTH: 338
<212> TYPE: PRT
<213> ORGANISM: Artificial Sequence
<220> FEATURE:
<223> OTHER INFORMATION: Synthetic polypeptide designated OSO

<400> SEQUENCE: 6

Ser Ser Thr Leu Ser Leu Pro Glu Ser Gly Pro Val Thr Ile Ile Pro
 1               5                  10                  15
```

-continued

```
Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Lys Cys Ala Asp Ser Asn Pro Arg Gly Val Ser Ala Tyr Leu
        115                 120                 125

Ser Arg Pro Ser Pro Phe Asp Leu Phe Ile Arg Lys Ser Pro Thr Ile
    130                 135                 140

Thr Cys Leu Val Val Asp Leu Ala Pro Ser Lys Gly Thr Val Asn Leu
145                 150                 155                 160

Thr Trp Ser Arg Ala Ser Gly Lys Pro Val Asn His Ser Thr Arg Lys
                165                 170                 175

Glu Glu Lys Gln Arg Asn Gly Thr Leu Thr Val Thr Ser Thr Leu Pro
            180                 185                 190

Val Gly Thr Arg Asp Trp Ile Glu Gly Glu Thr Tyr Gln Cys Arg Val
        195                 200                 205

Thr His Pro His Leu Pro Arg Ala Leu Met Arg Ser Thr Thr Lys Leu
    210                 215                 220

Ala Ser Pro Gly Lys Arg Leu Ala Pro Glu Val Tyr Met Leu Pro Pro
225                 230                 235                 240

Ser Pro Glu Glu Thr Gly Thr Thr Arg Thr Val Thr Cys Leu Ile Arg
                245                 250                 255

Gly Phe Tyr Pro Ser Glu Ile Ser Val Gln Trp Leu Phe Asn Asn Glu
            260                 265                 270

Glu Asp His Thr Gly His His Thr Thr Thr Arg Pro Gln Lys Asp His
        275                 280                 285

Gly Thr Asp Pro Ser Phe Phe Leu Tyr Ser Arg Met Leu Val Asn Lys
    290                 295                 300

Ser Ile Trp Glu Lys Gly Asn Leu Val Thr Cys Arg Val Val His Glu
305                 310                 315                 320

Ala Leu Pro Gly Ser Arg Thr Leu Glu Lys Ser Leu His Tyr Ser Ala
                325                 330                 335

Gly Asn
```

```
<210> SEQ ID NO 7
<211> LENGTH: 1665
<212> TYPE: DNA
<213> ORGANISM: Artificial Sequence
<220> FEATURE:
<223> OTHER INFORMATION: Insert sequence designated ORORO

<400> SEQUENCE: 7

tcgagtactt tatctctccc agaaagtggc cctgtgacaa tcatcccacc tacagtgaag      60

ctcttccact catcctgtga cccccgaggg gatgctcatt ccaccatcca gctgctctgc     120

cttgtctctg gcttctcccc agccaaggtc catgtgacct ggctggtaga tggacaggag     180

gctgaaaatc tctttcccta tacaaccaga cctaagaggg aagggggaca gactttttct     240
```

```
ctacaaagtg aagtcaacat cacacagggc cagtggatgt catcaaacac ctacacctgc    300

catgtcaagc acaatggcag catctttgaa gacagttcta gaagatgctc agatgatgag    360

ccccggggtg tgattaccta cctgatccca cccagtcccc tcgacctgta tgaaaatggg    420

actcccaaac ttacctgtct ggttttggac ctggaaagtg aggagaatat caccgtgacg    480

tgggtccgag agcgtaagaa gtctataggt tcggcatccc agaggagtac caagcaccat    540

aatgccacaa ccagtatcac ctccatcttg ccagtggatg ccaaggactg gatcgaaggt    600

gaaggctacc agtgcagagt ggaccaccct cactttccca agcccattgt gcgttccatc    660

accaagctta tcgatctccc agaaagtggc cctgtgacaa tcatcccacc tacagtgaag    720

ctcttccact catcctgtga cccccgaggg gatgctcatt ccaccatcca gctgctctgc    780

cttgtctctg gcttctcccc agccaaggtc catgtgacct ggctggtaga tggacaggag    840

gctgaaaatc tctttcccta tacaaccaga cctaagaggg aaggggggaca gactttttct    900

ctacaaagtg aagtcaacat cacacagggc cagtggatgt catcaaacac ctacacctgc    960

catgtcaagc acaatggcag catctttgaa gacagttcta gaagatgctc agatgatgag   1020

ccccggggtg tgattaccta cctgatccca cccagtcccc tcgacctgta tgaaaatggg   1080

actcccaaac ttacctgtct ggttttggac ctggaaagtg aggagaatat caccgtgacg   1140

tgggtccgag agcgtaagaa gtctataggt tcggcatccc agaggagtac caagcaccat   1200

aatgccacaa ccagtatcac ctccatcttg ccagtggatg ccaaggactg gatcgaaggt   1260

gaaggctacc agtgcagagt ggaccaccct cactttccca agcccattgt gcgttccatc   1320

accgctagcc caggcaaacg cttagccccc gaggtatata tgctccctcc atctccagag   1380

gaaacaggaa ccactcgcac tgtaacctgc ctaattcggg gtttctaccc ttctgaaata   1440

tctgtccaat ggctgtttaa taacgaagag gaccacactg gacaccatac taccacccgt   1500

ccccaaaagg accacggaac ggatccttcc ttcttcctct acagccgaat gcttgtcaac   1560

aagtctattt gggaaaaagg caatctcgtc acctgccgtg tggtgcatga agccctacct   1620

ggctcccgca ccctggaaaa aagcctgcat tactcagctg gtaac                   1665
```

```
<210> SEQ ID NO 8
<211> LENGTH: 555
<212> TYPE: PRT
<213> ORGANISM: Artificial Sequence
<220> FEATURE:
<223> OTHER INFORMATION: Synthetic polypeptide designated ORORO

<400> SEQUENCE: 8

Ser Ser Thr Leu Ser Leu Pro Glu Ser Gly Pro Val Thr Ile Ile Pro
 1               5                  10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110
```

-continued

```
Ser Arg Arg Cys Ser Asp Asp Glu Pro Arg Gly Val Ile Thr Tyr Leu
        115                 120                 125

Ile Pro Pro Ser Pro Leu Asp Leu Tyr Glu Asn Gly Thr Pro Lys Leu
    130                 135                 140

Thr Cys Leu Val Leu Asp Leu Glu Ser Glu Glu Asn Ile Thr Val Thr
145                 150                 155                 160

Trp Val Arg Glu Arg Lys Lys Ser Ile Gly Ser Ala Ser Gln Arg Ser
                165                 170                 175

Thr Lys His His Asn Ala Thr Thr Ser Ile Thr Ser Ile Leu Pro Val
            180                 185                 190

Asp Ala Lys Asp Trp Ile Glu Gly Glu Gly Tyr Gln Cys Arg Val Asp
        195                 200                 205

His Pro His Phe Pro Lys Pro Ile Val Arg Ser Ile Thr Lys Leu Ile
    210                 215                 220

Asp Leu Pro Glu Ser Gly Pro Val Thr Ile Ile Pro Pro Thr Val Lys
225                 230                 235                 240

Leu Phe His Ser Ser Cys Asp Pro Arg Gly Asp Ala His Ser Thr Ile
                245                 250                 255

Gln Leu Leu Cys Leu Val Ser Gly Phe Ser Pro Ala Lys Val His Val
            260                 265                 270

Thr Trp Leu Val Asp Gly Gln Glu Ala Glu Asn Leu Phe Pro Tyr Thr
        275                 280                 285

Thr Arg Pro Lys Arg Glu Gly Gly Gln Thr Phe Ser Leu Gln Ser Glu
    290                 295                 300

Val Asn Ile Thr Gln Gly Gln Trp Met Ser Ser Asn Thr Tyr Thr Cys
305                 310                 315                 320

His Val Lys His Asn Gly Ser Ile Phe Glu Asp Ser Ser Arg Arg Cys
                325                 330                 335

Ser Asp Asp Glu Pro Arg Gly Val Ile Thr Tyr Leu Ile Pro Pro Ser
            340                 345                 350

Pro Leu Asp Leu Tyr Glu Asn Gly Thr Pro Lys Leu Thr Cys Leu Val
        355                 360                 365

Leu Asp Leu Glu Ser Glu Glu Asn Ile Thr Val Thr Trp Val Arg Glu
    370                 375                 380

Arg Lys Lys Ser Ile Gly Ser Ala Ser Gln Arg Ser Thr Lys His His
385                 390                 395                 400

Asn Ala Thr Thr Ser Ile Thr Ser Ile Leu Pro Val Asp Ala Lys Asp
                405                 410                 415

Trp Ile Glu Gly Glu Gly Tyr Gln Cys Arg Val Asp His Pro His Phe
            420                 425                 430

Pro Lys Pro Ile Val Arg Ser Ile Thr Ala Ser Pro Gly Lys Arg Leu
        435                 440                 445

Ala Pro Glu Val Tyr Met Leu Pro Pro Ser Pro Glu Glu Thr Gly Thr
    450                 455                 460

Thr Arg Thr Val Thr Cys Leu Ile Arg Gly Phe Tyr Pro Ser Glu Ile
465                 470                 475                 480

Ser Val Gln Trp Leu Phe Asn Asn Glu Glu Asp His Thr Gly His His
                485                 490                 495

Thr Thr Thr Arg Pro Gln Lys Asp His Gly Thr Asp Pro Ser Phe Phe
            500                 505                 510

Leu Tyr Ser Arg Met Leu Val Asn Lys Ser Ile Trp Glu Lys Gly Asn
        515                 520                 525
```

-continued

```
Leu Val Thr Cys Arg Val Val His Glu Ala Leu Pro Gly Ser Arg Thr
    530                 535                 540

Leu Glu Lys Ser Leu His Tyr Ser Ala Gly Asn
545                 550                 555
```

<210> SEQ ID NO 9
<211> LENGTH: 1698
<212> TYPE: DNA
<213> ORGANISM: Artificial Sequence
<220> FEATURE:
<223> OTHER INFORMATION: Insert sequence designated modOSOSO-H

<400> SEQUENCE: 9

```
tcgagtactt tatctctccc agaaagtggc cctgtgacaa tcatcccacc tacagtgaag     60
ctcttccact catcctgtga cccccgaggg gatgctcatt ccaccatcca gctgctctgc    120
cttgtctctg gcttctcccc agccaaggtc catgtgacct ggctggtaga tggacaggag    180
gctgaaaatc tctttcccta tacaaccaga cctaagaggg aaggggggaca gactttttct    240
ctacaaagtg aagtcaacat cacacagggc cagtggatgt catcaaacac ctacacctgc    300
catgtcaagc acaatggcag catctttgaa gacagttcta gaaagtgtgc agattccaac    360
ccgagagggg tgagcgccta cctaagccgg cccagcccgt tcgacctgtt catccgcaag    420
tcgcccacga tcacctgtct ggtggtggac ctggcaccca gcaaggggac cgtgaacctg    480
acctggtccg aggcccaagg gaagcctgtg aaccactcca ccagaaagga ggagaagcag    540
cgcaatggca cgttaaccgt cacgtccacc ctgccggtgg gcacccgaga ctggatcgag    600
gggcgtacgt accagtgcag ggtgacccac ccccacctgc ccagggccct catgcggtcc    660
acgaccaagc ttatcgatat cccagaaagt ggccctgtga caatcatccc acctacagtg    720
aagctcttcc actcatcctg tgacccccga ggggatgctc attccaccat ccagctgctc    780
tgccttgtct ctggcttctc cccagccaag gtccatgtga cctggctggt agatggacag    840
gaggctgaaa atctctttcc ctatacaacc agacctaaga gggaaggggg acagactttt    900
tctctacaaa gtgaagtcaa catcacacag ggccagtgga tgtcatcaaa cacctacacc    960
tgccatgtca agcacaatgg cagcatcttt gaagacagtt ctagaaagtg tgcagattcc   1020
aacccgagag gggtgagcgc ctacctaagc cggcccagcc cgttcgacct gttcatccgc   1080
aagtcgccca cgatcacctg tctggtggtg gacctggcac ccagcaaggg gaccgtgaac   1140
ctgacctggt ccgaggccca agggaagcct gtgaaccact ccaccagaaa ggaggagaag   1200
cagcgcaatg gcacgttaac cgtcacgtcc accctgccgg tgggcacccg agactggatc   1260
gaggggcgta cgtaccagtg cagggtgacc cacccccacc tgcccagggc cctcatgcgg   1320
tccacgaccg ctagcccagg caaacgctta gcccccgagg tatatatgct ccctccatct   1380
ccagaggaaa caggaaccac tcgcactgta acctgcctaa ttcggggttt ctacccttct   1440
gaaatatctg tccaatggct gtttaataac gaagaggacc acactggaca ccatactacc   1500
acccgtcccc aaaaggacca cggaacggat ccttccttct tcctctacag ccgaatgctt   1560
gtcaacaagt ctatttggga aaaaggcaat ctcgtcacct gccgtgtggt gcatgaagcc   1620
ctacctggct cccgcaccct ggaaaaaagc ctgcattact cagctggtaa cggatcagga   1680
caccatcacc atcaccat                                                 1698
```

<210> SEQ ID NO 10
<211> LENGTH: 566
<212> TYPE: PRT
<213> ORGANISM: Artificial Sequence -continued
<220> FEATURE:
<223> OTHER INFORMATION: Synthetic polypeptide designated modOSOSO-H

<400> SEQUENCE: 10

```
Ser Ser Thr Leu Ser Leu Pro Glu Ser Gly Pro Val Thr Ile Ile Pro
 1               5                  10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Lys Cys Ala Asp Ser Asn Pro Arg Gly Val Ser Ala Tyr Leu
        115                 120                 125

Ser Arg Pro Ser Pro Phe Asp Leu Phe Ile Arg Lys Ser Pro Thr Ile
    130                 135                 140

Thr Cys Leu Val Val Asp Leu Ala Pro Ser Lys Gly Thr Val Asn Leu
145                 150                 155                 160

Thr Trp Ser Arg Ala Ser Gly Lys Pro Val Asn His Ser Thr Arg Lys
                165                 170                 175

Glu Glu Lys Gln Arg Asn Gly Thr Leu Thr Val Thr Ser Thr Leu Pro
            180                 185                 190

Val Gly Thr Arg Asp Trp Ile Glu Gly Glu Thr Tyr Gln Cys Arg Val
        195                 200                 205

Thr His Pro His Leu Pro Arg Ala Leu Met Arg Ser Thr Thr Lys Leu
    210                 215                 220

Ile Asp Ile Pro Glu Ser Gly Pro Val Thr Ile Ile Pro Pro Thr Val
225                 230                 235                 240

Lys Leu Phe His Ser Ser Cys Asp Pro Arg Gly Asp Ala His Ser Thr
                245                 250                 255

Ile Gln Leu Leu Cys Leu Val Ser Gly Phe Ser Pro Ala Lys Val His
            260                 265                 270

Val Thr Trp Leu Val Asp Gly Gln Glu Ala Glu Asn Leu Phe Pro Tyr
        275                 280                 285

Thr Thr Arg Pro Lys Arg Glu Gly Gly Gln Thr Phe Ser Leu Gln Ser
    290                 295                 300

Glu Val Asn Ile Thr Gln Gly Gln Trp Met Ser Ser Asn Thr Tyr Thr
305                 310                 315                 320

Cys His Val Lys His Asn Gly Ser Ile Phe Glu Asp Ser Ser Arg Lys
                325                 330                 335

Cys Ala Asp Ser Asn Pro Arg Gly Val Ser Ala Tyr Leu Ser Arg Pro
            340                 345                 350

Ser Pro Phe Asp Leu Phe Ile Arg Lys Ser Pro Thr Ile Thr Cys Leu
        355                 360                 365

Val Val Asp Leu Ala Pro Ser Lys Gly Thr Val Asn Leu Thr Trp Ser
    370                 375                 380

Arg Ala Ser Gly Lys Pro Val Asn His Ser Thr Arg Lys Glu Glu Lys
385                 390                 395                 400
```

-continued

```
Gln Arg Asn Gly Thr Leu Thr Val Thr Ser Thr Leu Pro Val Gly Thr
                405                 410                 415

Arg Asp Trp Ile Glu Gly Glu Thr Tyr Gln Cys Arg Val Thr His Pro
            420                 425                 430

His Leu Pro Arg Ala Leu Met Arg Ser Thr Thr Ala Ser Pro Gly Lys
        435                 440                 445

Arg Leu Ala Pro Glu Val Tyr Met Leu Pro Pro Ser Pro Glu Glu Thr
    450                 455                 460

Gly Thr Thr Arg Thr Val Thr Cys Leu Ile Arg Gly Phe Tyr Pro Ser
465                 470                 475                 480

Glu Ile Ser Val Gln Trp Leu Phe Asn Asn Glu Glu Asp His Thr Gly
                485                 490                 495

His His Thr Thr Thr Arg Pro Gln Lys Asp His Gly Thr Asp Pro Ser
            500                 505                 510

Phe Phe Leu Tyr Ser Arg Met Leu Val Asn Lys Ser Ile Trp Glu Lys
        515                 520                 525

Gly Asn Leu Val Thr Cys Arg Val Val His Glu Ala Leu Pro Gly Ser
    530                 535                 540

Arg Thr Leu Glu Lys Ser Leu His Tyr Ser Ala Gly Asn Gly Ser Gly
545                 550                 555                 560

His His His His His His
                565
```

<210> SEQ ID NO 11
<211> LENGTH: 1671
<212> TYPE: DNA
<213> ORGANISM: Artificial Sequence
<220> FEATURE:
<223> OTHER INFORMATION: Insert sequence designated modOSOSO

<400> SEQUENCE: 11

```
tcgagtactt tatctctccc agaaagtggc cctgtgacaa tcatcccacc tacagtgaag     60

ctcttccact catcctgtga cccccgaggg gatgctcatt ccaccatcca gctgctctgc    120

cttgtctctg gcttctcccc agccaaggtc catgtgacct ggctggtaga tggacaggag    180

gctgaaaatc tctttcccta tacaaccaga cctaagaggg aaggggggaca gacttttct    240

ctacaaagtg aagtcaacat cacacagggc cagtggatgt catcaaacac ctacacctgc    300

catgtcaagc acaatggcag catctttgaa gacagttcta gaaagtgtgc agattccaac    360

ccgagagggg tgagcgccta cctaagccgg cccagcccgt tcgacctgtt catccgcaag    420

tcgcccacga tcacctgtct ggtggtggac ctggcaccca gcaaggggac cgtgaacctg    480

acctggtccg aggcccaagg gaagcctgtg aaccactcca ccagaaagga ggagaagcag    540

cgcaatggca cgttaaccgt cacgtccacc ctgccggtgg gcacccgaga ctggatcgag    600

ggcgtacgt accagtgcag ggtgacccac ccccacctgc ccagggccct catgcggtcc    660

acgaccaagc ttatcgatat cccagaaagt ggccctgtga caatcatccc acctacagtg    720

aagctcttcc actcatcctg tgacccccga ggggatgctc attccaccat ccagctgctc    780

tgccttgtct ctggcttctc cccagccaag gtccatgtga cctggctggt agatggacag    840

gaggctgaaa atctctttcc ctatacaacc agacctaaga gggaaggggg acagactttt    900

tctctacaaa gtgaagtcaa catcacacag ggccagtgga tgtcatcaaa cacctacacc    960

tgccatgtca agcacaatgg cagcatcttt gaagacagtt ctagaaagtg tgcagattcc   1020

aacccgagag ggtgagcgc ctacctaagc cggcccagcc cgttcgacct gttcatccgc   1080
```

```
aagtcgccca cgatcacctg tctggtggtg gacctggcac ccagcaaggg gaccgtgaac   1140

ctgacctggt ccgaggccca agggaagcct gtgaaccact ccaccagaaa ggaggagaag   1200

cagcgcaatg gcacgttaac cgtcacgtcc accctgccgg tgggcacccg agactggatc   1260

gaggggcgta cgtaccagtg cagggtgacc cacccccacc tgcccagggc cctcatgcgg   1320

tccacgaccg ctagcccagg caaacgctta gcccccgagg tatatatgct ccctccatct   1380

ccagaggaaa caggaaccac tcgcactgta acctgcctaa ttcggggttt ctacccttct   1440

gaaatatctg tccaatggct gtttaataac gaagaggacc acactggaca ccatactacc   1500

acccgtcccc aaaaggacca cggaacggat ccttccttct tcctctacag ccgaatgctt   1560

gtcaacaagt ctatttggga aaaaggcaat ctcgtcacct gccgtgtggt gcatgaagcc   1620

ctacctggct cccgcaccct ggaaaaaagc ctgcattact cagctggtaa c            1671
```

```
<210> SEQ ID NO 12
<211> LENGTH: 557
<212> TYPE: PRT
<213> ORGANISM: Artificial Sequence
<220> FEATURE:
<223> OTHER INFORMATION: Synthetic polypeptide designated modOSOSO

<400> SEQUENCE: 12

Ser Ser Thr Leu Ser Leu Pro Glu Ser Gly Pro Val Thr Ile Ile Pro
 1               5                  10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Lys Cys Ala Asp Ser Asn Pro Arg Gly Val Ser Ala Tyr Leu
        115                 120                 125

Ser Arg Pro Ser Pro Phe Asp Leu Phe Ile Arg Lys Ser Pro Thr Ile
    130                 135                 140

Thr Cys Leu Val Val Asp Leu Ala Pro Ser Lys Gly Thr Val Asn Leu
145                 150                 155                 160

Thr Trp Ser Arg Ala Ser Gly Lys Pro Val Asn His Ser Thr Arg Lys
                165                 170                 175

Glu Glu Lys Gln Arg Asn Gly Thr Leu Thr Val Thr Ser Thr Leu Pro
            180                 185                 190

Val Gly Thr Arg Asp Trp Ile Glu Gly Glu Thr Tyr Gln Cys Arg Val
        195                 200                 205

Thr His Pro His Leu Pro Arg Ala Leu Met Arg Ser Thr Thr Lys Leu
    210                 215                 220

Ile Asp Ile Pro Glu Ser Gly Pro Val Thr Ile Ile Pro Pro Thr Val
225                 230                 235                 240

Lys Leu Phe His Ser Ser Cys Asp Pro Arg Gly Asp Ala His Ser Thr
                245                 250                 255
```

-continued

```
Ile Gln Leu Leu Cys Leu Val Ser Gly Phe Ser Pro Ala Lys Val His
            260                 265                 270

Val Thr Trp Leu Val Asp Gly Gln Glu Ala Glu Asn Leu Phe Pro Tyr
        275                 280                 285

Thr Thr Arg Pro Lys Arg Glu Gly Gly Gln Thr Phe Ser Leu Gln Ser
    290                 295                 300

Glu Val Asn Ile Thr Gln Gly Gln Trp Met Ser Ser Asn Thr Tyr Thr
305                 310                 315                 320

Cys His Val Lys His Asn Gly Ser Ile Phe Glu Asp Ser Ser Arg Lys
                325                 330                 335

Cys Ala Asp Ser Asn Pro Arg Gly Val Ser Ala Tyr Leu Ser Arg Pro
            340                 345                 350

Ser Pro Phe Asp Leu Phe Ile Arg Lys Ser Pro Thr Ile Thr Cys Leu
        355                 360                 365

Val Val Asp Leu Ala Pro Ser Lys Gly Thr Val Asn Leu Thr Trp Ser
    370                 375                 380

Arg Ala Ser Gly Lys Pro Val Asn His Ser Thr Arg Lys Glu Glu Lys
385                 390                 395                 400

Gln Arg Asn Gly Thr Leu Thr Val Thr Ser Thr Leu Pro Val Gly Thr
                405                 410                 415

Arg Asp Trp Ile Glu Gly Glu Thr Tyr Gln Cys Arg Val Thr His Pro
            420                 425                 430

His Leu Pro Arg Ala Leu Met Arg Ser Thr Thr Ala Ser Pro Gly Lys
        435                 440                 445

Arg Leu Ala Pro Glu Val Tyr Met Leu Pro Pro Ser Pro Glu Glu Thr
    450                 455                 460

Gly Thr Thr Arg Thr Val Thr Cys Leu Ile Arg Gly Phe Tyr Pro Ser
465                 470                 475                 480

Glu Ile Ser Val Gln Trp Leu Phe Asn Asn Glu Glu Asp His Thr Gly
                485                 490                 495

His His Thr Thr Thr Arg Pro Gln Lys Asp His Gly Thr Asp Pro Ser
            500                 505                 510

Phe Phe Leu Tyr Ser Arg Met Leu Val Asn Lys Ser Ile Trp Glu Lys
        515                 520                 525

Gly Asn Leu Val Thr Cys Arg Val Val His Glu Ala Leu Pro Gly Ser
    530                 535                 540

Arg Thr Leu Glu Lys Ser Leu His Tyr Ser Ala Gly Asn
545                 550                 555
```

<210> SEQ ID NO 13
<211> LENGTH: 1041
<212> TYPE: DNA
<213> ORGANISM: Artificial Sequence
<220> FEATURE:
<223> OTHER INFORMATION: Insert sequence designated OSO-H

<400> SEQUENCE: 13

```
tcgagtactt tatctctccc agaaagtggc cctgtgacaa tcatcccacc tacagtgaag     60

ctcttccact catcctgtga cccccgaggg gatgctcatt ccaccatcca gctgctctgc    120

cttgtctctg gcttctcccc agccaaggtc catgtgacct ggctggtaga tggacaggag    180

gctgaaaatc tctttcccta tacaaccaga cctaagaggg aagggggaca gactttttct    240

ctacaaagtg aagtcaacat cacacagggc cagtggatgt catcaaacac ctacacctgc    300

catgtcaagc acaatggcag catctttgaa gacagttcta gaaagtgtgc agattccaac    360
```

-continued

```
ccgagagggg tgagcgccta cctaagccgg cccagcccgt tcgacctgtt catccgcaag    420

tcgcccacga tcacctgtct ggtggtggac ctggcaccca gcaaggggac cgtgaacctg    480

acctggtccc gggccagtgg gaagcctgtg aaccactcca ccagaaagga ggagaagcag    540

cgcaatggca cgttaaccgt cacgtccacc ctgccggtgg gcacccgaga ctggatcgag    600

ggggagacct accagtgcag ggtgacccac ccccacctgc ccagggccct catgcggtcc    660

acgaccaagc ttgctagccc aggcaaacgc ttagcccccg aggtatatat gctccctcca    720

tctccagagg aaacaggaac cactcgcact gtaacctgcc taattcgggg tttctaccct    780

tctgaaatat ctgtccaatg gctgtttaat aacgaagagg accacactgg acaccatact    840

accacccgtc cccaaaagga ccacggaacg gatccttcct tcttcctcta cagccgaatg    900

cttgtcaaca agtctatttg ggaaaaaggc aatctcgtca cctgccgtgt ggtgcatgaa    960

gccctacctg gctcccgcac cctggaaaaa agcctgcatt actcagctgg taacggatca   1020

ggacaccatc accatcacca t                                              1041
```

<210> SEQ ID NO 14
<211> LENGTH: 347
<212> TYPE: PRT
<213> ORGANISM: Artificial Sequence
<220> FEATURE:
<223> OTHER INFORMATION: Synthetic polypeptide designated OSO-H

<400> SEQUENCE: 14

```
Ser Ser Thr Leu Ser Leu Pro Glu Ser Gly Pro Val Thr Ile Ile Pro
 1               5                  10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Lys Cys Ala Asp Ser Asn Pro Arg Gly Val Ser Ala Tyr Leu
        115                 120                 125

Ser Arg Pro Ser Pro Phe Asp Leu Phe Ile Arg Lys Ser Pro Thr Ile
    130                 135                 140

Thr Cys Leu Val Val Asp Leu Ala Pro Ser Lys Gly Thr Val Asn Leu
145                 150                 155                 160

Thr Trp Ser Arg Ala Ser Gly Lys Pro Val Asn His Ser Thr Arg Lys
                165                 170                 175

Glu Glu Lys Gln Arg Asn Gly Thr Leu Thr Val Thr Ser Thr Leu Pro
            180                 185                 190

Val Gly Thr Arg Asp Trp Ile Glu Gly Glu Thr Tyr Gln Cys Arg Val
        195                 200                 205

Thr His Pro His Leu Pro Arg Ala Leu Met Arg Ser Thr Thr Lys Leu
    210                 215                 220

Ala Ser Pro Gly Lys Arg Leu Ala Pro Glu Val Tyr Met Leu Pro Pro
225                 230                 235                 240
```

-continued

```
Ser Pro Glu Glu Thr Gly Thr Thr Arg Thr Val Thr Cys Leu Ile Arg
                245                 250                 255

Gly Phe Tyr Pro Ser Glu Ile Ser Val Gln Trp Leu Phe Asn Asn Glu
            260                 265                 270

Glu Asp His Thr Gly His His Thr Thr Thr Arg Pro Gln Lys Asp His
        275                 280                 285

Gly Thr Asp Pro Ser Phe Phe Leu Tyr Ser Arg Met Leu Val Asn Lys
    290                 295                 300

Ser Ile Trp Glu Lys Gly Asn Leu Val Thr Cys Arg Val Val His Glu
305                 310                 315                 320

Ala Leu Pro Gly Ser Arg Thr Leu Glu Lys Ser Leu His Tyr Ser Ala
                325                 330                 335

Gly Asn Gly Ser Gly His His His His His His
            340                 345
```

<210> SEQ ID NO 15
<211> LENGTH: 1671
<212> TYPE: DNA
<213> ORGANISM: Artificial Sequence
<220> FEATURE:
<223> OTHER INFORMATION: Insert sequence designated OSOSO

<400> SEQUENCE: 15

```
tcgagtactt tatctctccc agaaagtggc cctgtgacaa tcatcccacc tacagtgaag     60

ctcttccact catcctgtga cccccgaggg gatgctcatt ccaccatcca gctgctctgc    120

cttgtctctg gcttctcccc agccaaggtc catgtgacct ggctggtaga tggacaggag    180

gctgaaaatc tctttcccta tacaaccaga cctaagaggg aaggggggaca gactttttct    240

ctacaaagtg aagtcaacat cacacagggc cagtggatgt catcaaacac ctacacctgc    300

catgtcaagc acaatggcag catctttgaa gacagttcta gaaagtgtgc agattccaac    360

ccgagagggg tgagcgccta cctaagccgg cccagcccgt tcgacctgtt catccgcaag    420

tcgcccacga tcacctgtct ggtggtggac ctggcaccca gcaaggggac cgtgaacctg    480

acctggtccc gggccagtgg gaagcctgtg aaccactcca ccagaaagga ggagaagcag    540

cgcaatggca cgttaaccgt cacgtccacc ctgccggtgg gcacccgaga ctggatcgag    600

ggggagacct accagtgcag ggtgacccac ccccacctgc ccagggccct catgcggtcc    660

acgaccaagc ttatcgatat cccagaaagt ggccctgtga caatcatccc acctacagtg    720

aagctcttcc actcatcctg tgacccccga ggggatgctc attccaccat ccagctgctc    780

tgccttgtct ctggcttctc cccagccaag gtccatgtga cctggctggt agatggacag    840

gaggctgaaa atctctttcc ctatacaacc agacctaaga gggaaggggg acagactttt    900

tctctacaaa gtgaagtcaa catcacacag ggccagtgga tgtcatcaaa cacctacacc    960

tgccatgtca agcacaatgg cagcatcttt gaagacagtt ctagaaagtg tgcagattcc   1020

aacccgagag gggtgagcgc ctacctaagc cggcccagcc cgttcgacct gttcatccgc   1080

aagtcgccca cgatcacctg tctggtggtg gacctggcac ccagcaaggg gaccgtgaac   1140

ctgacctggt cccgggccag tgggaagcct gtgaaccact ccaccagaaa ggaggagaag   1200

cagcgcaatg gcacgttaac cgtcacgtcc accctgccgg tgggcacccg agactggatc   1260

gagggggaga cctaccagtg cagggtgacc cacccccacc tgcccagggc cctcatgcgg   1320

tccacgaccg ctagcccagg caaacgctta gcccccgagg tatatatgct ccctccatct   1380

ccagaggaaa caggaaccac tcgcactgta acctgcctaa ttcggggttt ctacccttct   1440
```

-continued

```
gaaatatctg tccaatggct gtttaataac gaagaggacc acactggaca ccatactacc   1500

acccgtcccc aaaaggacca cggaacggat ccttccttct tcctctacag ccgaatgctt   1560

gtcaacaagt ctatttggga aaaaggcaat ctcgtcacct gccgtgtggt gcatgaagcc   1620

ctacctggct cccgcaccct ggaaaaaagc ctgcattact cagctggtaa c            1671


<210> SEQ ID NO 16
<211> LENGTH: 557
<212> TYPE: PRT
<213> ORGANISM: Artificial Sequence
<220> FEATURE:
<223> OTHER INFORMATION: Synthetic polypeptide designated OSOSO

<400> SEQUENCE: 16

Ser Ser Thr Leu Ser Leu Pro Glu Ser Gly Pro Val Thr Ile Ile Pro
1               5                   10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Lys Cys Ala Asp Ser Asn Pro Arg Gly Val Ser Ala Tyr Leu
        115                 120                 125

Ser Arg Pro Ser Pro Phe Asp Leu Phe Ile Arg Lys Ser Pro Thr Ile
    130                 135                 140

Thr Cys Leu Val Val Asp Leu Ala Pro Ser Lys Gly Thr Val Asn Leu
145                 150                 155                 160

Thr Trp Ser Arg Ala Ser Gly Lys Pro Val Asn His Ser Thr Arg Lys
                165                 170                 175

Glu Glu Lys Gln Arg Asn Gly Thr Leu Thr Val Thr Ser Thr Leu Pro
            180                 185                 190

Val Gly Thr Arg Asp Trp Ile Glu Gly Glu Thr Tyr Gln Cys Arg Val
        195                 200                 205

Thr His Pro His Leu Pro Arg Ala Leu Met Arg Ser Thr Thr Lys Leu
    210                 215                 220

Ile Asp Ile Pro Glu Ser Gly Pro Val Thr Ile Ile Pro Pro Thr Val
225                 230                 235                 240

Lys Leu Phe His Ser Ser Cys Asp Pro Arg Gly Asp Ala His Ser Thr
                245                 250                 255

Ile Gln Leu Leu Cys Leu Val Ser Gly Phe Ser Pro Ala Lys Val His
            260                 265                 270

Val Thr Trp Leu Val Asp Gly Gln Glu Ala Glu Asn Leu Phe Pro Tyr
        275                 280                 285

Thr Thr Arg Pro Lys Arg Glu Gly Gly Gln Thr Phe Ser Leu Gln Ser
    290                 295                 300

Glu Val Asn Ile Thr Gln Gly Gln Trp Met Ser Ser Asn Thr Tyr Thr
305                 310                 315                 320

Cys His Val Lys His Asn Gly Ser Ile Phe Glu Asp Ser Ser Arg Lys
```

-continued

```
                325                 330                 335

Cys Ala Asp Ser Asn Pro Arg Gly Val Ser Ala Tyr Leu Ser Arg Pro
            340                 345                 350

Ser Pro Phe Asp Leu Phe Ile Arg Lys Ser Pro Thr Ile Thr Cys Leu
        355                 360                 365

Val Val Asp Leu Ala Pro Ser Lys Gly Thr Val Asn Leu Thr Trp Ser
    370                 375                 380

Arg Ala Ser Gly Lys Pro Val Asn His Ser Thr Arg Lys Glu Glu Lys
385                 390                 395                 400

Gln Arg Asn Gly Thr Leu Thr Val Thr Ser Thr Leu Pro Val Gly Thr
                405                 410                 415

Arg Asp Trp Ile Glu Gly Glu Thr Tyr Gln Cys Arg Val Thr His Pro
            420                 425                 430

His Leu Pro Arg Ala Leu Met Arg Ser Thr Thr Ala Ser Pro Gly Lys
        435                 440                 445

Arg Leu Ala Pro Glu Val Tyr Met Leu Pro Pro Ser Pro Glu Glu Thr
    450                 455                 460

Gly Thr Thr Arg Thr Val Thr Cys Leu Ile Arg Gly Phe Tyr Pro Ser
465                 470                 475                 480

Glu Ile Ser Val Gln Trp Leu Phe Asn Asn Glu Glu Asp His Thr Gly
                485                 490                 495

His His Thr Thr Thr Arg Pro Gln Lys Asp His Gly Thr Asp Pro Ser
            500                 505                 510

Phe Phe Leu Tyr Ser Arg Met Leu Val Asn Lys Ser Ile Trp Glu Lys
        515                 520                 525

Gly Asn Leu Val Thr Cys Arg Val Val His Glu Ala Leu Pro Gly Ser
    530                 535                 540

Arg Thr Leu Glu Lys Ser Leu His Tyr Ser Ala Gly Asn
545                 550                 555
```

```
<210> SEQ ID NO 17
<211> LENGTH: 1698
<212> TYPE: DNA
<213> ORGANISM: Artificial Sequence
<220> FEATURE:
<223> OTHER INFORMATION: Insert sequence designated OSOSO-H

<400> SEQUENCE: 17

tcgagtactt tatctctccc agaaagtggc cctgtgacaa tcatcccacc tacagtgaag      60

ctcttccact catcctgtga cccccgaggg gatgctcatt ccaccatcca gctgctctgc     120

cttgtctctg gcttctcccc agccaaggtc catgtgacct ggctggtaga tggacaggag     180

gctgaaaatc tctttcccta tacaaccaga cctaagaggg aaggggggaca gacttttttct   240

ctacaaagtg aagtcaacat cacacagggc cagtggatgt catcaaacac ctacacctgc     300

catgtcaagc acaatggcag catctttgaa gacagttcta gaaagtgtgc agattccaac     360

ccgagagggg tgagcgccta cctaagccgg cccagcccgt tcgacctgtt catccgcaag     420

tcgcccacga tcacctgtct ggtggtggac ctggcaccca gcaaggggac cgtgaacctg     480

acctggtccc gggccagtgg gaagcctgtg aaccactcca ccagaaagga ggagaagcag     540

cgcaatggca cgttaaccgt cacgtccacc ctgccggtgg gcacccgaga ctggatcgag     600

gggggagacct accagtgcag ggtgacccac ccccacctgc ccagggccct catgcggtcc    660

acgaccaagc ttatcgatat cccagaaagt ggccctgtga caatcatccc acctacagtg     720

aagctcttcc actcatcctg tgacccccga ggggatgctc attccaccat ccagctgctc     780
```

```
tgccttgtct ctggcttctc cccagccaag gtccatgtga cctggctggt agatggacag    840

gaggctgaaa atctctttcc ctatacaacc agacctaaga gggaaggggg acagactttt    900

tctctacaaa gtgaagtcaa catcacacag ggccagtgga tgtcatcaaa cacctacacc    960

tgccatgtca agcacaatgg cagcatcttt gaagacagtt ctagaaagtg tgcagattcc   1020

aacccgagag ggtgagcgc ctacctaagc cggcccagcc cgttcgacct gttcatccgc   1080

aagtcgccca cgatcacctg tctggtggtg gacctggcac ccagcaaggg gaccgtgaac   1140

ctgacctggt cccgggccag tgggaagcct gtgaaccact ccaccagaaa ggaggagaag   1200

cagcgcaatg gcacgttaac cgtcacgtcc accctgccgg tgggcacccg agactggatc   1260

gagggggaga cctaccagtg cagggtgacc cacccccacc tgcccagggc cctcatgcgg   1320

tccacgaccg ctagcccagg caaacgctta gcccccgagg tatatatgct ccctccatct   1380

ccagaggaaa caggaaccac tcgcactgta acctgcctaa ttcggggttt ctacccttct   1440

gaaatatctg tccaatggct gtttaataac gaagaggacc acactggaca ccatactacc   1500

acccgtcccc aaaaggacca cggaacggat ccttccttct tcctctacag ccgaatgctt   1560

gtcaacaagt ctatttggga aaaaggcaat ctcgtcacct gccgtgtggt gcatgaagcc   1620

ctacctggct cccgcaccct ggaaaaaagc ctgcattact cagctggtaa cggatcagga   1680

caccatcacc atcaccat                                                 1698
```

```
<210> SEQ ID NO 18
<211> LENGTH: 566
<212> TYPE: PRT
<213> ORGANISM: Artificial Sequence
<220> FEATURE:
<223> OTHER INFORMATION: Synthetic polypeptide designated OSOSO-H

<400> SEQUENCE: 18

Ser Ser Thr Leu Ser Leu Pro Glu Ser Gly Pro Val Thr Ile Ile Pro
 1               5                  10                  15

Pro Thr Val Lys Leu Phe His Ser Ser Cys Asp Pro Arg Gly Asp Ala
            20                  25                  30

His Ser Thr Ile Gln Leu Leu Cys Leu Val Ser Gly Phe Ser Pro Ala
        35                  40                  45

Lys Val His Val Thr Trp Leu Val Asp Gly Gln Glu Ala Glu Asn Leu
    50                  55                  60

Phe Pro Tyr Thr Thr Arg Pro Lys Arg Glu Gly Gly Gln Thr Phe Ser
65                  70                  75                  80

Leu Gln Ser Glu Val Asn Ile Thr Gln Gly Gln Trp Met Ser Ser Asn
                85                  90                  95

Thr Tyr Thr Cys His Val Lys His Asn Gly Ser Ile Phe Glu Asp Ser
            100                 105                 110

Ser Arg Lys Cys Ala Asp Ser Asn Pro Arg Gly Val Ser Ala Tyr Leu
        115                 120                 125

Ser Arg Pro Ser Pro Phe Asp Leu Phe Ile Arg Lys Ser Pro Thr Ile
    130                 135                 140

Thr Cys Leu Val Val Asp Leu Ala Pro Ser Lys Gly Thr Val Asn Leu
145                 150                 155                 160

Thr Trp Ser Arg Ala Ser Gly Lys Pro Val Asn His Ser Thr Arg Lys
                165                 170                 175

Glu Glu Lys Gln Arg Asn Gly Thr Leu Thr Val Thr Ser Thr Leu Pro
            180                 185                 190
```

-continued

```
Val Gly Thr Arg Asp Trp Ile Glu Gly Glu Thr Tyr Gln Cys Arg Val
        195                 200                 205

Thr His Pro His Leu Pro Arg Ala Leu Met Arg Ser Thr Thr Lys Leu
    210                 215                 220

Ile Asp Ile Pro Glu Ser Gly Pro Val Thr Ile Ile Pro Pro Thr Val
225                 230                 235                 240

Lys Leu Phe His Ser Ser Cys Asp Pro Arg Gly Asp Ala His Ser Thr
                245                 250                 255

Ile Gln Leu Leu Cys Leu Val Ser Gly Phe Ser Pro Ala Lys Val His
            260                 265                 270

Val Thr Trp Leu Val Asp Gly Gln Glu Ala Glu Asn Leu Phe Pro Tyr
        275                 280                 285

Thr Thr Arg Pro Lys Arg Glu Gly Gly Gln Thr Phe Ser Leu Gln Ser
    290                 295                 300

Glu Val Asn Ile Thr Gln Gly Gln Trp Met Ser Ser Asn Thr Tyr Thr
305                 310                 315                 320

Cys His Val Lys His Asn Gly Ser Ile Phe Glu Asp Ser Ser Arg Lys
                325                 330                 335

Cys Ala Asp Ser Asn Pro Arg Gly Val Ser Ala Tyr Leu Ser Arg Pro
            340                 345                 350

Ser Pro Phe Asp Leu Phe Ile Arg Lys Ser Pro Thr Ile Thr Cys Leu
        355                 360                 365

Val Val Asp Leu Ala Pro Ser Lys Gly Thr Val Asn Leu Thr Trp Ser
    370                 375                 380

Arg Ala Ser Gly Lys Pro Val Asn His Ser Thr Arg Lys Glu Glu Lys
385                 390                 395                 400

Gln Arg Asn Gly Thr Leu Thr Val Thr Ser Thr Leu Pro Val Gly Thr
                405                 410                 415

Arg Asp Trp Ile Glu Gly Glu Thr Tyr Gln Cys Arg Val Thr His Pro
            420                 425                 430

His Leu Pro Arg Ala Leu Met Arg Ser Thr Thr Ala Ser Pro Gly Lys
        435                 440                 445

Arg Leu Ala Pro Glu Val Tyr Met Leu Pro Pro Ser Pro Glu Glu Thr
    450                 455                 460

Gly Thr Thr Arg Thr Val Thr Cys Leu Ile Arg Gly Phe Tyr Pro Ser
465                 470                 475                 480

Glu Ile Ser Val Gln Trp Leu Phe Asn Asn Glu Glu Asp His Thr Gly
                485                 490                 495

His His Thr Thr Thr Arg Pro Gln Lys Asp His Gly Thr Asp Pro Ser
            500                 505                 510

Phe Phe Leu Tyr Ser Arg Met Leu Val Asn Lys Ser Ile Trp Glu Lys
        515                 520                 525

Gly Asn Leu Val Thr Cys Arg Val Val His Glu Ala Leu Pro Gly Ser
    530                 535                 540

Arg Thr Leu Glu Lys Ser Leu His Tyr Ser Ala Gly Asn Gly Ser Gly
545                 550                 555                 560

His His His His His His
                565
```

<210> SEQ ID NO 19
<211> LENGTH: 27
<212> TYPE: DNA
<213> ORGANISM: Artificial Sequence
<220> FEATURE:
<223> OTHER INFORMATION: Primer -continued

```
<400> SEQUENCE: 19

aactcgagta ctttatctct cccagaa                                         27


<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20

atctcgagat tagttaccag ctgagtaatg ca                                   32
```